US008882728B2

(12) United States Patent
Harders et al.

(10) Patent No.: US 8,882,728 B2
(45) Date of Patent: Nov. 11, 2014

(54) IMPLANTABLE INJECTION PORT

(75) Inventors: James A. Harders, Goleta, CA (US); Joseph S. Raven, Santa Barbara, CA (US); Dimitrios Stroumpoulis, Goleta, CA (US); Nikhil S. Trilokekar, Goleta, CA (US)

(73) Assignee: Apollo Endosurgery, Inc., Austin, TX (US)

( * ) Notice: Subject to any disclaimer, the term of this patent is extended or adjusted under 35 U.S.C. 154(b) by 786 days.

(21) Appl. No.: 12/703,515

(22) Filed: Feb. 10, 2010

(65) Prior Publication Data

US 2011/0196394 A1 Aug. 11, 2011

(51) Int. Cl.

| | |
|---|---|
| ***A61M 31/00*** | (2006.01) |
| ***A61F 5/00*** | (2006.01) |
| *A61M 39/02* | (2006.01) |

(52) U.S. Cl.

CPC ...... *A61F 5/0043* (2013.01); *A61M 2039/0223* (2013.01); *A61F 5/003* (2013.01); *A61M 39/0208* (2013.01); *A61F 5/0056* (2013.01)

USPC ........................................ 604/288.04; 600/37

(58) Field of Classification Search

CPC ..... A61F 5/0056; A61M 25/02; A61M 25/04; A61M 2025/0095; A61M 2025/0286; A61M 39/0208; A61M 39/04; A61M 2039/0223

USPC .......... 604/174, 175, 288.01–288.04; 600/37; 606/140, 141, 151, 157

See application file for complete search history.

(56) References Cited

U.S. PATENT DOCUMENTS

| | | | |
|---|---|---|---|
| 586,113 | A | 7/1897 | Bott |
| 2,163,048 | A | 6/1939 | McKee |
| 2,737,954 | A | 3/1956 | Knapp |
| 3,371,352 | A | 3/1968 | Siposs et al. |
| 3,569,660 | A | 3/1971 | Houldcroft |
| 3,587,115 | A | 6/1971 | Shiley |
| 3,596,660 | A | 8/1971 | Melone |
| 3,667,081 | A | 6/1972 | Burger |

(Continued)

FOREIGN PATENT DOCUMENTS

| | | |
|---|---|---|
| CN | 1250382 | 4/2000 |
| CN | 1367670 | 9/2002 |

(Continued)

OTHER PUBLICATIONS

Helioscopie Product Insert for Heliogast, pp. 1-11 (undated).

(Continued)

*Primary Examiner* — Kami A Bosworth

(74) *Attorney, Agent, or Firm* — Gordon & Jacobson, PC

(57) ABSTRACT

An implantable injection port facilitates filling and/or draining an inflatable portion of a gastric band. In an embodiment, the port comprises a movable cap that causes anchor wires to extend from anchor devices in order to implant the injection port in the tissue of a patient. In another embodiment, the port comprises a handle that rotates to implant curved anchors into the tissue of a patient. In yet another embodiment, a cap is configured to move towards a base of the port in order to cause the curved anchors to rotate into the tissue of a patient. The cap may also rotate with respect to the base in order to lock the cap and the anchors in position. Further, surfaces of the injection port may be textured to increase adhesiveness to the patient's tissue during installation and to facilitate simpler installation.

8 Claims, 13 Drawing Sheets

114
105
110
132
113
113
135
133
134
130
112
120
120
120
120

134
105
114
134
110
132
133
112
130
125
125
120
120
125
120

(56) References Cited

U.S. PATENT DOCUMENTS 3,688,764 A 9/1972 Reed
3,840,018 A 10/1974 Heifetz
3,958,562 A 5/1976 Hakim et al.
3,971,376 A 7/1976 Wichterle
4,019,499 A 4/1977 Fitzgerald
4,118,805 A 10/1978 Reimels
4,151,835 A 5/1979 Showell et al.
4,161,943 A 7/1979 Nogier
4,164,943 A 8/1979 Hill et al.
4,190,040 A 2/1980 Schulte
4,233,992 A 11/1980 Bisping
4,265,252 A 5/1981 Chubbuck et al.
4,280,722 A 7/1981 Guptil et al.
4,413,985 A 11/1983 Wellner et al.
4,474,572 A 10/1984 McNaughton et al.
4,502,335 A 3/1985 Wamstad et al.
4,543,088 A 9/1985 Bootman et al.
4,557,722 A 12/1985 Harris
4,559,043 A * 12/1985 Whitehouse et al. ......... 604/201
4,569,675 A 2/1986 Prosl et al.
4,588,394 A 5/1986 Schulte et al.
4,592,339 A 6/1986 Kuzmak et al.
4,592,355 A 6/1986 Antebi
4,634,427 A 1/1987 Hannula et al.
4,655,765 A 4/1987 Swift
4,673,394 A 6/1987 Fenton, Jr. et al.
4,692,146 A 9/1987 Hilger
4,696,288 A 9/1987 Kuzmak et al.
4,704,103 A 11/1987 Stober et al.
4,710,174 A 12/1987 Moden et al.
4,738,657 A 4/1988 Hancock et al.
4,767,410 A 8/1988 Moden et al.
4,772,270 A 9/1988 Wiita et al.
4,778,452 A 10/1988 Moden et al.
4,781,680 A 11/1988 Redmond et al.
4,796,641 A 1/1989 Mills et al.
4,802,885 A 2/1989 Weeks et al.
4,832,054 A 5/1989 Bark
4,840,615 A 6/1989 Hancock et al.
4,850,227 A 7/1989 Luettgen et al.
4,858,623 A 8/1989 Bradshaw et al.
4,861,341 A 8/1989 Woodburn
4,881,939 A 11/1989 Newman
4,886,501 A 12/1989 Johnston et al.
4,902,278 A 2/1990 Maget et al.
4,904,241 A 2/1990 Bark
4,913,702 A 4/1990 Yum et al.
4,915,690 A 4/1990 Cone et al.
4,929,230 A 5/1990 Pfleger
4,929,236 A 5/1990 Sampson
4,966,588 A 10/1990 Rayman et al.
4,967,755 A 11/1990 Pohndorf
4,978,338 A 12/1990 Melsky et al.
5,006,115 A 4/1991 McDonald
5,013,298 A 5/1991 Moden et al.
5,026,344 A 6/1991 Dijkstra et al.
5,041,098 A 8/1991 Loiterman et al.
5,045,060 A 9/1991 Melsky et al.
5,074,868 A 12/1991 Kuzmak
5,090,954 A 2/1992 Geary
5,092,897 A 3/1992 Forte
5,094,244 A 3/1992 Callahan et al.
5,108,377 A 4/1992 Cone et al.
5,125,408 A 6/1992 Basser
5,133,753 A 7/1992 Bark et al.
5,137,529 A 8/1992 Watson et al.
5,147,483 A 9/1992 Melsky et al.
5,152,747 A 10/1992 Olivier
5,167,638 A 12/1992 Felix et al.
5,185,003 A 2/1993 Brethauer
5,207,644 A 5/1993 Strecker
5,213,574 A 5/1993 Tucker
5,226,429 A 7/1993 Kuzmak
5,226,894 A 7/1993 Haber et al.
5,250,026 A 10/1993 Ehrlich et al.
5,273,537 A 12/1993 Haskvitz et al.
5,281,205 A 1/1994 McPherson
5,284,479 A 2/1994 de Jong
5,318,545 A 6/1994 Tucker
5,336,194 A 8/1994 Polaschegg et al.
5,337,747 A 8/1994 Neftel
5,360,407 A 11/1994 Leonard et al.
5,368,040 A 11/1994 Carney
5,387,192 A 2/1995 Glantz et al.
5,391,164 A 2/1995 Giampapa
5,449,368 A 9/1995 Kuzmak
5,476,460 A 12/1995 Montalvo
5,514,174 A 5/1996 Heil, Jr. et al.
5,540,648 A 7/1996 Yoon
5,556,388 A 9/1996 Johlin, Jr.
5,558,641 A 9/1996 Glantz et al.
5,562,617 A 10/1996 Finch, Jr. et al.
5,571,104 A 11/1996 Li
5,575,777 A 11/1996 Cover et al.
5,601,604 A 2/1997 Vincent
5,637,102 A 6/1997 Tolkoff et al.
5,653,755 A 8/1997 Ledergerber
5,658,298 A 8/1997 Vincent et al.
5,674,397 A 10/1997 Pawlak et al.
5,683,447 A 11/1997 Bush et al.
5,688,237 A 11/1997 Rozga et al.
5,695,490 A 12/1997 Flaherty et al.
5,716,342 A 2/1998 Dumbraveanu et al.
5,718,682 A 2/1998 Tucker
5,722,957 A 3/1998 Steinbach
5,748,200 A 5/1998 Funahashi
5,810,735 A 9/1998 Halperin et al.
5,814,019 A 9/1998 Steinbach et al.
5,833,654 A 11/1998 Powers et al.
5,843,033 A 12/1998 Ropiak
RE36,176 E 3/1999 Kuzmak
5,883,654 A 3/1999 Katsuyama
5,902,598 A 5/1999 Chen et al.
5,906,596 A 5/1999 Tallarida
5,910,149 A 6/1999 Kuzmak
5,911,704 A 6/1999 Humes
5,931,829 A 8/1999 Burbank et al.
5,932,460 A 8/1999 Mills et al.
5,935,083 A 8/1999 Williams
5,938,669 A 8/1999 Klaiber et al.
5,951,512 A 9/1999 Dalton
6,024,704 A 2/2000 Meador et al.
6,030,369 A 2/2000 Engelson et al.
6,039,712 A 3/2000 Fogarty et al.
6,074,341 A 6/2000 Anderson et al.
6,090,066 A 7/2000 Schnell
6,098,405 A 8/2000 Miyata et al.
6,102,678 A 8/2000 Peclat
6,102,922 A 8/2000 Jakobsson et al.
6,123,700 A 9/2000 Mills et al.
6,152,885 A 11/2000 Taepke
6,171,252 B1 1/2001 Roberts
6,183,449 B1 2/2001 Sibbitt
6,213,973 B1 4/2001 Eliasen et al.
6,221,024 B1 4/2001 Miesel
6,234,973 B1 5/2001 Meador et al.
6,258,079 B1 7/2001 Burbank et al.
6,264,676 B1 7/2001 Gellman et al.
6,270,475 B1 8/2001 Bestetti et al.
6,283,949 B1 9/2001 Roorda
6,321,124 B1 11/2001 Cigaina
6,349,740 B1 2/2002 Cho et al.
6,432,040 B1 8/2002 Meah
6,450,946 B1 9/2002 Forsell
6,453,907 B1 9/2002 Forsell
6,454,699 B1 9/2002 Forsell
6,459,917 B1 10/2002 Gowda et al.
6,461,293 B1 10/2002 Forsell
6,464,628 B1 10/2002 Forsell
6,470,213 B1 10/2002 Alley
6,470,892 B1 10/2002 Forsell
6,478,783 B1 11/2002 Moorehead
6,511,490 B2 1/2003 Robert
6,547,801 B1 4/2003 Dargent et al.

(56) References Cited

U.S. PATENT DOCUMENTS

| | | | | |
|---|---|---|---|---|
| 6,572,587 | B2 | 6/2003 | Lerman et al. | |
| 6,589,184 | B2 | 7/2003 | Noren et al. | |
| 6,648,849 | B2 | 11/2003 | Tenhuisen et al. | |
| 6,666,845 | B2 | 12/2003 | Hooper et al. | |
| 6,689,100 | B2 | 2/2004 | Connelly et al. | |
| 6,723,053 | B2 | 4/2004 | Ackerman et al. | |
| 6,733,519 | B2 | 5/2004 | Lashinski et al. | |
| 6,792,309 | B1 | 9/2004 | Noren | |
| 6,810,880 | B1 | 11/2004 | Jennings, Jr. et al. | |
| 6,813,964 | B1 | 11/2004 | Clark et al. | |
| 6,860,857 | B2 | 3/2005 | Noren et al. | |
| 6,915,162 | B2 | 7/2005 | Noren et al. | |
| 6,921,267 | B2 | 7/2005 | van Oostrom et al. | |
| 6,929,631 | B1 | 8/2005 | Brugger et al. | |
| 6,939,299 | B1 | 9/2005 | Petersen et al. | |
| 6,953,444 | B2 | 10/2005 | Rosenberg | |
| 6,964,204 | B2 | 11/2005 | Clark et al. | |
| 6,966,875 | B1 | 11/2005 | Longobardi | |
| 6,997,914 | B2 | 2/2006 | Smith et al. | |
| 7,017,583 | B2 | 3/2006 | Forsell | |
| 7,020,531 | B1 | 3/2006 | Colliou et al. | |
| 7,056,286 | B2 | 6/2006 | Ravenscroft et al. | |
| 7,063,669 | B2 | 6/2006 | Brawner et al. | |
| 7,073,387 | B2 | 7/2006 | Zdeblick et al. | |
| 7,082,843 | B2 | 8/2006 | Clark et al. | |
| 7,103,418 | B2 * | 9/2006 | Laske et al. | 607/120 |
| 7,131,945 | B2 | 11/2006 | Fink et al. | |
| 7,144,400 | B2 | 12/2006 | Byrum et al. | |
| 7,149,587 | B2 | 12/2006 | Wardle et al. | |
| 7,191,007 | B2 | 3/2007 | Desai et al. | |
| 7,195,774 | B2 | 3/2007 | Carvalho et al. | |
| 7,223,239 | B2 | 5/2007 | Schulze et al. | |
| 7,226,419 | B2 | 6/2007 | Lane et al. | |
| 7,261,003 | B2 | 8/2007 | McDonald et al. | |
| 7,267,645 | B2 | 9/2007 | Anderson et al. | |
| 7,282,023 | B2 | 10/2007 | Frering | |
| 7,311,716 | B2 | 12/2007 | Byrum | |
| 7,311,717 | B2 | 12/2007 | Egle | |
| 7,351,198 | B2 | 4/2008 | Byrum et al. | |
| 7,351,226 | B1 | 4/2008 | Herskowitz | |
| 7,351,240 | B2 | 4/2008 | Hassler, Jr. et al. | |
| 7,353,747 | B2 | 4/2008 | Swayze et al. | |
| 7,364,542 | B2 | 4/2008 | Jambor et al. | |
| 7,367,937 | B2 | 5/2008 | Jambor et al. | |
| 7,374,557 | B2 | 5/2008 | Conlon et al. | |
| 7,374,565 | B2 | 5/2008 | Hassler, Jr. et al. | |
| 7,390,294 | B2 | 6/2008 | Hassler, Jr. | |
| 7,413,547 | B1 | 8/2008 | Lichtscheidl et al. | |
| 7,416,528 | B2 | 8/2008 | Crawford et al. | |
| 7,437,951 | B2 | 10/2008 | McDonald et al. | |
| 7,438,718 | B2 | 10/2008 | Milliman et al. | |
| 7,445,614 | B2 | 11/2008 | Bunodiere et al. | |
| 7,468,038 | B2 | 12/2008 | Ye et al. | |
| 7,500,944 | B2 | 3/2009 | Byrum et al. | |
| 7,510,530 | B2 | 3/2009 | Hashimoto et al. | |
| 7,530,943 | B2 | 5/2009 | Lechner | |
| 7,553,298 | B2 | 6/2009 | Hunt et al. | |
| 7,561,916 | B2 | 7/2009 | Hunt et al. | |
| 7,580,746 | B2 | 8/2009 | Gilkerson et al. | |
| 7,591,185 | B1 | 9/2009 | Mothilal et al. | |
| 7,593,777 | B2 | 9/2009 | Gerber | |
| 7,634,319 | B2 | 12/2009 | Schneider et al. | |
| 7,651,483 | B2 | 1/2010 | Byrum et al. | |
| 7,658,196 | B2 | 2/2010 | Ferreri et al. | |
| 7,699,770 | B2 | 4/2010 | Hassler, Jr. et al. | |
| 7,708,722 | B2 | 5/2010 | Glenn | |
| 7,762,998 | B2 | 7/2010 | Birk et al. | |
| 7,762,999 | B2 | 7/2010 | Byrum | |
| 7,775,215 | B2 | 8/2010 | Hassler, Jr. et al. | |
| 7,775,966 | B2 | 8/2010 | Dlugos et al. | |
| 7,811,275 | B2 | 10/2010 | Birk et al. | |
| 7,850,660 | B2 | 12/2010 | Uth et al. | |
| 7,862,546 | B2 | 1/2011 | Conlon et al. | |
| 7,909,754 | B2 | 3/2011 | Hassler, Jr. et al. | |
| 7,909,804 | B2 | 3/2011 | Stats | |
| 8,007,474 | B2 | 8/2011 | Uth et al. | |
| 2001/0052141 | A1 | 12/2001 | Andersen | |
| 2002/0013545 | A1 | 1/2002 | Soltanpour et al. | |
| 2002/0058969 | A1 | 5/2002 | Noren et al. | |
| 2002/0087147 | A1 | 7/2002 | Hooper et al. | |
| 2002/0095181 | A1 | 7/2002 | Beyar | |
| 2002/0139208 | A1 | 10/2002 | Yatskov | |
| 2002/0198548 | A1 | 12/2002 | Robert | |
| 2003/0045800 | A1 | 3/2003 | Noren et al. | |
| 2003/0045910 | A1 | 3/2003 | Sorensen et al. | |
| 2003/0073880 | A1 | 4/2003 | Polsky et al. | |
| 2003/0078506 | A1 | 4/2003 | Noren et al. | |
| 2003/0139690 | A1 | 7/2003 | Aebli et al. | |
| 2004/0064110 | A1 | 4/2004 | Forsell | |
| 2004/0065615 | A1 | 4/2004 | Hooper et al. | |
| 2004/0068233 | A1 | 4/2004 | DiMatteo | |
| 2004/0082908 | A1 | 4/2004 | Whitehurst et al. | |
| 2004/0111050 | A1 | 6/2004 | Smedley et al. | |
| 2004/0204692 | A1 | 10/2004 | Eliasen | |
| 2004/0254536 | A1 | 12/2004 | Conlon et al. | |
| 2004/0254537 | A1 | 12/2004 | Conlon et al. | |
| 2004/0260229 | A1 | 12/2004 | Meir | |
| 2004/0260319 | A1 | 12/2004 | Egle | |
| 2004/0267288 | A1 | 12/2004 | Byrum et al. | |
| 2004/0267291 | A1 | 12/2004 | Byrum et al. | |
| 2004/0267292 | A1 | 12/2004 | Byrum et al. | |
| 2004/0267293 | A1 | 12/2004 | Byrum et al. | |
| 2004/0267377 | A1 | 12/2004 | Egle | |
| 2005/0010177 | A1 | 1/2005 | Tsai | |
| 2005/0045060 | A1 | 3/2005 | Forbes et al. | |
| 2005/0049578 | A1 | 3/2005 | Tu et al. | |
| 2005/0070875 | A1 | 3/2005 | Kulessa | |
| 2005/0070937 | A1 | 3/2005 | Jambor et al. | |
| 2005/0085778 | A1 | 4/2005 | Parks | |
| 2005/0092093 | A1 | 5/2005 | Kang et al. | |
| 2005/0131325 | A1 | 6/2005 | Chen et al. | |
| 2005/0131352 | A1 | 6/2005 | Conlon et al. | |
| 2005/0131383 | A1 | 6/2005 | Chen et al. | |
| 2005/0148956 | A1 | 7/2005 | Conlon et al. | |
| 2005/0149143 | A1 | 7/2005 | Libbus et al. | |
| 2005/0209573 | A1 | 9/2005 | Brugger et al. | |
| 2005/0240155 | A1 | 10/2005 | Conlon | |
| 2005/0240156 | A1 | 10/2005 | Conlon | |
| 2005/0267500 | A1 | 12/2005 | Hassler, Jr. et al. | |
| 2005/0277899 | A1 | 12/2005 | Conlon et al. | |
| 2005/0283041 | A1 | 12/2005 | Egle | |
| 2005/0283118 | A1 | 12/2005 | Uth et al. | |
| 2005/0283119 | A1 | 12/2005 | Uth et al. | |
| 2006/0074439 | A1 | 4/2006 | Garner et al. | |
| 2006/0122578 | A1 | 6/2006 | Lord et al. | |
| 2006/0161186 | A1 | 7/2006 | Hassler, Jr. et al. | |
| 2006/0173423 | A1 | 8/2006 | Conlon | |
| 2006/0173424 | A1 | 8/2006 | Conlon | |
| 2006/0178647 | A1 | 8/2006 | Stats | |
| 2006/0178648 | A1 | 8/2006 | Barron et al. | |
| 2006/0184141 | A1 | 8/2006 | Smith et al. | |
| 2006/0189887 | A1 | 8/2006 | Hassler, Jr. et al. | |
| 2006/0189888 | A1 | 8/2006 | Hassler, Jr. et al. | |
| 2006/0190039 | A1 | 8/2006 | Birk et al. | |
| 2006/0199997 | A1 | 9/2006 | Hassler, Jr. et al. | |
| 2006/0211912 | A1 | 9/2006 | Dlugos et al. | |
| 2006/0211913 | A1 | 9/2006 | Dlugos et al. | |
| 2006/0211914 | A1 | 9/2006 | Hassler, Jr. et al. | |
| 2006/0217668 | A1 | 9/2006 | Schulze et al. | |
| 2006/0217673 | A1 | 9/2006 | Schulze et al. | |
| 2006/0235445 | A1 | 10/2006 | Birk et al. | |
| 2006/0235448 | A1 | 10/2006 | Roslin et al. | |
| 2006/0247539 | A1 | 11/2006 | Schugt et al. | |
| 2006/0266128 | A1 | 11/2006 | Clark et al. | |
| 2006/0293625 | A1 | 12/2006 | Hunt et al. | |
| 2006/0293626 | A1 | 12/2006 | Byrum et al. | |
| 2006/0293627 | A1 | 12/2006 | Byrum et al. | |
| 2006/0293628 | A1 | 12/2006 | Hunt et al. | |
| 2007/0010790 | A1 | 1/2007 | Byrum et al. | |
| 2007/0015954 | A1 | 1/2007 | Dlugos | |
| 2007/0015955 | A1 | 1/2007 | Tsonton | |
| 2007/0016231 | A1 | 1/2007 | Jambor et al. | |
| 2007/0027356 | A1 | 2/2007 | Ortiz | |
| 2007/0038255 | A1 | 2/2007 | Kieval et al. | |

(56) References Cited

U.S. PATENT DOCUMENTS

| | | | |
|---|---|---|---|
| 2007/0060959 | A1 | 3/2007 | Salo et al. |
| 2007/0073250 | A1 | 3/2007 | Schneiter |
| 2007/0078391 | A1 | 4/2007 | Wortley et al. |
| 2007/0088336 | A1 | 4/2007 | Dalton |
| 2007/0088391 | A1 | 4/2007 | McAlexander et al. |
| 2007/0129765 | A1 | 6/2007 | Gilkerson et al. |
| 2007/0135758 | A1 | 6/2007 | Childers et al. |
| 2007/0149947 | A1 | 6/2007 | Byrum |
| 2007/0156013 | A1 | 7/2007 | Birk |
| 2007/0158769 | A1 | 7/2007 | You |
| 2007/0161958 | A1 | 7/2007 | Glenn |
| 2007/0167672 | A1 | 7/2007 | Dlugos et al. |
| 2007/0173685 | A1 | 7/2007 | Jambor et al. |
| 2007/0185462 | A1 | 8/2007 | Byrum |
| 2007/0191717 | A1 | 8/2007 | Rosen et al. |
| 2007/0205384 | A1 | 9/2007 | Kurosawa |
| 2007/0208313 | A1 | 9/2007 | Conlon et al. |
| 2007/0213837 | A1 | 9/2007 | Ferreri et al. |
| 2007/0219510 | A1 | 9/2007 | Zinn et al. |
| 2007/0235083 | A1 | 10/2007 | Dlugos |
| 2007/0250086 | A1 | 10/2007 | Wiley et al. |
| 2007/0255165 | A1 | 11/2007 | Uesugi et al. |
| 2007/0255234 | A1 | 11/2007 | Haase et al. |
| 2007/0265666 | A1 | 11/2007 | Roberts et al. |
| 2007/0282196 | A1 | 12/2007 | Birk et al. |
| 2007/0293829 | A1 | 12/2007 | Conlon et al. |
| 2008/0009680 | A1 | 1/2008 | Hassler, Jr. |
| 2008/0015406 | A1 | 1/2008 | Dlugos et al. |
| 2008/0039772 | A1 | 2/2008 | Chantriaux et al. |
| 2008/0058632 | A1 | 3/2008 | Tai et al. |
| 2008/0097496 | A1 | 4/2008 | Chang et al. |
| 2008/0114308 | A1 | 5/2008 | di Palma et al. |
| 2008/0119798 | A1 | 5/2008 | Chantriaux et al. |
| 2008/0243093 | A1 | 10/2008 | Kalpin et al. |
| 2008/0249806 | A1 | 10/2008 | Dlugos et al. |
| 2008/0250340 | A1 | 10/2008 | Dlugos et al. |
| 2008/0250341 | A1 | 10/2008 | Dlugos et al. |
| 2008/0255403 | A1 | 10/2008 | Voegele et al. |
| 2008/0255414 | A1 | 10/2008 | Voegele et al. |
| 2008/0255425 | A1 | 10/2008 | Voegele et al. |
| 2008/0255459 | A1 | 10/2008 | Voegele et al. |
| 2008/0255537 | A1 | 10/2008 | Voegele et al. |
| 2008/0281412 | A1 | 11/2008 | Smith et al. |
| 2008/0287969 | A1 | 11/2008 | Tsonton et al. |
| 2008/0287974 | A1 | 11/2008 | Widenhouse et al. |
| 2008/0312553 | A1 | 12/2008 | Timmons |
| 2008/0319435 | A1 | 12/2008 | Rioux et al. |
| 2009/0018608 | A1 | 1/2009 | Schwartz et al. |
| 2009/0048524 | A1 | 2/2009 | Wildau et al. |
| 2009/0054914 | A1 | 2/2009 | Lechner |
| 2009/0062825 | A1 | 3/2009 | Pool et al. |
| 2009/0071258 | A1 | 3/2009 | Kouda et al. |
| 2009/0076466 | A1 | 3/2009 | Quebbemann et al. |
| 2009/0082757 | A1 | 3/2009 | Rogers et al. |
| 2009/0082793 | A1 | 3/2009 | Birk |
| 2009/0093768 | A1 | 4/2009 | Conlon et al. |
| 2009/0099538 | A1 | 4/2009 | Paganon |
| 2009/0105735 | A1 | 4/2009 | Stam et al. |
| 2009/0112308 | A1 | 4/2009 | Kassem |
| 2009/0118572 | A1 | 5/2009 | Lechner |
| 2009/0149874 | A1 | 6/2009 | Ortiz et al. |
| 2009/0157106 | A1 | 6/2009 | Marcotte et al. |
| 2009/0157107 | A1 | 6/2009 | Kierath et al. |
| 2009/0157113 | A1 | 6/2009 | Marcotte et al. |
| 2009/0171375 | A1 | 7/2009 | Coe et al. |
| 2009/0171378 | A1 | 7/2009 | Coe et al. |
| 2009/0171379 | A1 | 7/2009 | Coe et al. |
| 2009/0192404 | A1 | 7/2009 | Ortiz et al. |
| 2009/0192415 | A1 | 7/2009 | Ortiz et al. |
| 2009/0192533 | A1 | 7/2009 | Dlugos, Jr. et al. |
| 2009/0192534 | A1 | 7/2009 | Ortiz et al. |
| 2009/0192541 | A1 | 7/2009 | Ortiz et al. |
| 2009/0198261 | A1 | 8/2009 | Schweikert |
| 2009/0202387 | A1 | 8/2009 | Dlugos, Jr. et al. |
| 2009/0204131 | A1 | 8/2009 | Ortiz et al. |
| 2009/0204132 | A1 | 8/2009 | Ortiz et al. |
| 2009/0209995 | A1 | 8/2009 | Byrum et al. |
| 2009/0216255 | A1 | 8/2009 | Coe et al. |
| 2009/0221974 | A1 | 9/2009 | Paganon |
| 2009/0222031 | A1 | 9/2009 | Axelsson |
| 2009/0222065 | A1 | 9/2009 | Dlugos, Jr. et al. |
| 2009/0227862 | A1 | 9/2009 | Smith et al. |
| 2009/0228028 | A1 | 9/2009 | Coe et al. |
| 2009/0228072 | A1 | 9/2009 | Coe et al. |
| 2009/0248125 | A1 | 10/2009 | Brostrom |
| 2009/0248126 | A1 | 10/2009 | Nippoldt et al. |
| 2009/0254052 | A1 | 10/2009 | Birk et al. |
| 2009/0259190 | A1 | 10/2009 | Birk et al. |
| 2009/0259191 | A1 | 10/2009 | Birk et al. |
| 2009/0259231 | A1 | 10/2009 | Birk et al. |
| 2009/0264901 | A1 | 10/2009 | Franklin et al. |
| 2009/0270904 | A1 | 10/2009 | Birk et al. |
| 2009/0299216 | A1 | 12/2009 | Chen et al. |
| 2009/0299672 | A1 | 12/2009 | Zhang et al. |
| 2009/0306462 | A1 | 12/2009 | Lechner |
| 2009/0308169 | A1 | 12/2009 | Mothilal et al. |
| 2010/0087843 | A1 | 4/2010 | Bertolote et al. |
| 2010/0100079 | A1 | 4/2010 | Berkcan et al. |
| 2010/0114149 | A1 | 5/2010 | Albrecht et al. |
| 2010/0125249 | A1 * | 5/2010 | Rosenberg et al. ........... 604/175 |
| 2010/0130941 | A1 | 5/2010 | Conlon et al. |
| 2010/0152532 | A1 | 6/2010 | Marcotte |
| 2010/0191271 | A1 | 7/2010 | Lau et al. |
| 2010/0211085 | A1 | 8/2010 | Uth et al. |
| 2010/0217198 | A1 | 8/2010 | Franklin et al. |
| 2010/0217199 | A1 | 8/2010 | Uth et al. |
| 2010/0217200 | A1 | 8/2010 | Uth et al. |
| 2010/0228080 | A1 | 9/2010 | Tavori et al. |
| 2010/0234808 | A1 | 9/2010 | Uth et al. |
| 2011/0054407 | A1 | 3/2011 | Olroyd et al. |
| 2011/0082426 | A1 | 4/2011 | Conlon et al. |

FOREIGN PATENT DOCUMENTS

| | | |
|---|---|---|
| DE | 3927001 | 2/1991 |
| DE | 4211045 | 10/1993 |
| DE | 19751791 | 5/1997 |
| DE | 19745654 | 4/1999 |
| EP | 0343910 | 11/1989 |
| EP | 0611561 | 9/1993 |
| EP | 0858814 | 8/1998 |
| EP | 0867197 | 9/1998 |
| EP | 1057457 | 12/2000 |
| EP | 1346753 | 9/2003 |
| EP | 1396242 | 3/2004 |
| EP | 1396243 | 3/2004 |
| EP | 1488824 | 12/2004 |
| EP | 1543861 | 6/2005 |
| EP | 1547643 | 6/2005 |
| EP | 1591140 | 11/2005 |
| EP | 1736194 | 12/2006 |
| EP | 1736195 | 12/2006 |
| EP | 1736196 | 12/2006 |
| EP | 1736197 | 12/2006 |
| EP | 1736198 | 12/2006 |
| EP | 1736199 | 12/2006 |
| EP | 1870126 | 12/2007 |
| EP | 1985263 | 10/2008 |
| EP | 2070494 | 6/2009 |
| EP | 2095798 | 9/2009 |
| FR | 2740977 | 5/1997 |
| FR | 2797181 | 2/2001 |
| FR | 2823663 | 10/2002 |
| FR | 2851168 | 8/2004 |
| FR | 2855744 | 12/2004 |
| FR | 2916980 | 12/2008 |
| JP | 2119877 | 5/1990 |
| JP | 8107934 | 4/1996 |
| SU | 1823791 | 6/1991 |
| WO | WO 92/20519 | 11/1992 |
| WO | WO 94/22520 | 10/1994 |

(56) References Cited

FOREIGN PATENT DOCUMENTS

| | | |
|---|---|---|
| WO | WO 96/40357 | 12/1996 |
| WO | WO 97/01370 | 1/1997 |
| WO | WO 99/20338 | 4/1999 |
| WO | WO 99/26543 | 6/1999 |
| WO | WO 99/34859 | 7/1999 |
| WO | WO 00/15158 | 3/2000 |
| WO | WO 00/33901 | 6/2000 |
| WO | WO 01/10359 | 2/2001 |
| WO | WO 01/49245 | 7/2001 |
| WO | WO 01/80926 | 11/2001 |
| WO | WO 01/95813 | 12/2001 |
| WO | WO 02/10667 | 2/2002 |
| WO | WO 02/74381 | 9/2002 |
| WO | WO 03/105732 | 12/2003 |
| WO | WO 2004/016971 | 3/2004 |
| WO | WO 2005/037055 | 4/2005 |
| WO | WO 2005/072627 | 8/2005 |
| WO | WO 2006/021695 | 3/2006 |
| WO | WO 2009/007526 | 1/2009 |
| WO | WO 2009/129474 | 10/2009 |

OTHER PUBLICATIONS http://en/wikipedia.org/Injection_Molding.

Autumn K. et al.; "Evidence of Van Der Waals Adhesion in Gecko Setae"; Pnas; vol. 99; No. 19; pp. 12252-12256; Sep. 17, 2012.

Geim AK. et al.; "Microfabricated Adhesive Mimicking Gecko Foot-Hair"; Nature Materials Abstract only; vol. 2; No. 7; 2003.

Yamagami, Takuji; "Technical Developments: Use of Targeting Guide Wire in Left Subclavian Puncture During Percutaneous Implantation of Port-Catheter Systems Using the Catheter Tip Fixation Method" European Radiology; vol. 13; pp. 863-866; 2003.

Yurdumakan B., et al.; "Synthetic Gecko Foot-Hairs from Multiwalled Carbon Nanotubes"; The Royal Society of Chemistry; p. 3799-3801; 2005.

Autumn K., et al.: Evidence of Van Der Waals Adhesion in Gecko Setae. PNAS (2002); 99(19): p. 12252-12256.

Geim Ak., et al.: Mircrofabricated Advhesive Mimicking Gecko Foot-Hair. Nature Materials. (2003) 2: p. 461-463.

Yurdumakan B., et al.: Synthetic Gecko Foot-Hairs from Multiwalled Carbon Nanotubes. The Royal Society of Chemistry. (2005) : p. 3799-3801.

* cited by examiner 210
255
253
240
262
263
245
247
247
257
241
242
249
259
250
265

IMPLANTABLE INJECTION PORT

FIELD OF THE INVENTION

The present invention generally relates to medical systems and apparatus and uses thereof for treating obesity and/or obesity-related diseases, and more specifically, relates to gastric banding systems that utilize an injection port that is implantable, typically laparoscopically.

BACKGROUND

Adjustable gastric banding apparatus have provided an effective and substantially less invasive alternative to gastric bypass surgery and other conventional surgical weight loss procedures. Despite the positive outcomes of invasive weight loss procedures, such as gastric bypass surgery, it has been recognized that sustained weight loss can be achieved through a laparoscopically-placed gastric band, for example, the LAP-BAND® (Allergan, Inc., Irvine, Calif.) gastric band or the LAP-BAND AP® (Allergan, Inc., Irvine, Calif.) gastric band. Generally, gastric bands are placed about the cardia, or upper portion, of a patient's stomach forming a stoma that restricts food's passage into a lower portion of the stomach. When the stoma is of an appropriate size that is restricted by a gastric band, food held in the upper portion of the stomach provides a feeling of satiety or fullness that discourages overeating. Unlike gastric bypass procedures, gastric band apparatus are reversible and require no permanent modification to the gastrointestinal tract.

Over time, a stoma created by a gastric band may need adjustment in order to maintain an appropriate size, which is neither too restrictive nor too passive. Accordingly, prior art gastric band systems provide a subcutaneous fluid access port connected to an expandable or inflatable portion of the gastric band. By adding fluid to or removing fluid from the inflatable portion by means of a hypodermic needle inserted into the access port, the effective size of the gastric band can be adjusted to provide a tighter or looser constriction.

Some existing access ports are connected to the rectus muscle sheath using sutures. Suturing these access ports may be difficult because of the obesity of the patient who is receiving the gastric band. For example, the ports are generally placed below several centimeters of fatty tissue which increases the difficulty of suturing the port.

Some existing access ports may be implanted without using sutures. However, these sutureless ports generally require specialized tools to activate the implanting mechanisms. Such specialized tools increase the cost of the sutureless ports. Thus, injection ports that may be implanted laparoscopically without sutures and/or additional specialized tools are disclosed herein.

SUMMARY

Generally described herein are implantable injection ports for gastric banding systems, and methods of use thereof. The apparatus, systems and methods described herein aid in facilitating obesity control and/or treating obesity-related diseases.

In an embodiment, an implantable injection port for use in conjunction with a gastric band and for attaching to bodily tissue comprises a base with a first opening. The port also comprises a cap with a handle, and the cap is moveable, using the handle, between an undeployed position and a deployed position. Further, the cap is spaced apart from the base when it is in the deployed position. The port includes a self sealing, needle-penetrable material to facilitate filling and/or draining the gastric band.

Additionally, the port comprises a first anchor positioned in the first opening of the base, and the first anchor has a cavity, a hole, an inner shaft, and an anchor wire. The inner shaft is coupled to the cap such that moving the cap from the undeployed position to the deployed position causes a portion of the anchor wire to move through the hole and to be positioned outside the cavity. Moving the cap from the deployed position to the undeployed position causes a portion of the anchor wire to move through the hole to be positioned inside the cavity. A locking rod may be utilized to lock the cap in the deployed position.

In accordance with an embodiment, the port has a press-fit and/or interference-fit fitting for securing the handle adjacent to the cap. For example, the cap may have a center opening and an outer portion surrounding the center opening, and the fitting may be located in this outer portion. Also, the base may have a center opening and an outer portion surrounding the center opening, and the fitting may be located in this outer portion of the base.

In accordance with another embodiment, an implantable injection port comprises a body having a first opening and a handle attached to the body. The handle is moveable between a detached position and an attached position. The port further comprises a first anchor device positioned in the first opening of the body, and the first anchor device is attached to the handle such that moving the handle from the detached position to the attached position causes a portion of the first anchor device to move through the first opening. As the needle moves through the opening, it is positioned outside the body of the port. Moving the handle from the attached position to the detached position causes a portion of the first anchor device to move through the first opening to be positioned inside the body of the port.

Further, in accordance with an embodiment, an implantable injection port comprises a base and a curved anchor attached to a handle that is rotatably attached to the base. When the handle is rotated, the curved anchor moves to an implanted position. The port further comprises a quick-connect and strain relief fitting coupled to a reservoir disposed in the base. The base of the port may further comprise a suture tab to facilitate attaching the port to a patient. The quick-connect and strain relief fitting may be configured to interface with gastric band tubing that connects the gastric band to the reservoir.

Another embodiment of an implantable injection port comprises a cap and a base coupled to the cap. The base has a first textured surface that provides adhesiveness between the base and a contact surface. The port further comprises a hook rotatably disposed within the base, and when the cap moves towards the base, the hook moves to an implanted position.

In various embodiments, the cap may have an engagement surface, and the base may be configured to nest within the cap. An internal ring is attached to the base and the hook is rotatably connected to the internal ring. The hook is configured to move through a slot in the base from an undeployed position to a deployed position when the cap moves toward the base. Such movement facilitates implanting the injection port in tissue of a patient. The port further comprises a locking mechanism in the cap, and rotating the cap with respect to the base causes the locking mechanism to engage the hook to lock the hook in place and to prevent the cap from moving with respect to the base.

In various embodiments, a surface of the implantable injection port may comprise a textured surface. For example, the base, cap, and/or other surface may be textured to facilitate implanting of the port. Various textures such as parallel wavy lines and/or micro-papillae may be utilized.

DETAILED DESCRIPTION

The present invention generally relates to implantable injection ports for gastric banding systems, for example, for treatment of obesity and obesity related conditions. The injection ports may be implanted without using specialized implantation equipment, except for laparoscopic tools. For example, a doctor's thumb and/or fingers may be utilized to implant the injection port. Standard forceps or hemostats may also be used.

Figure 1:
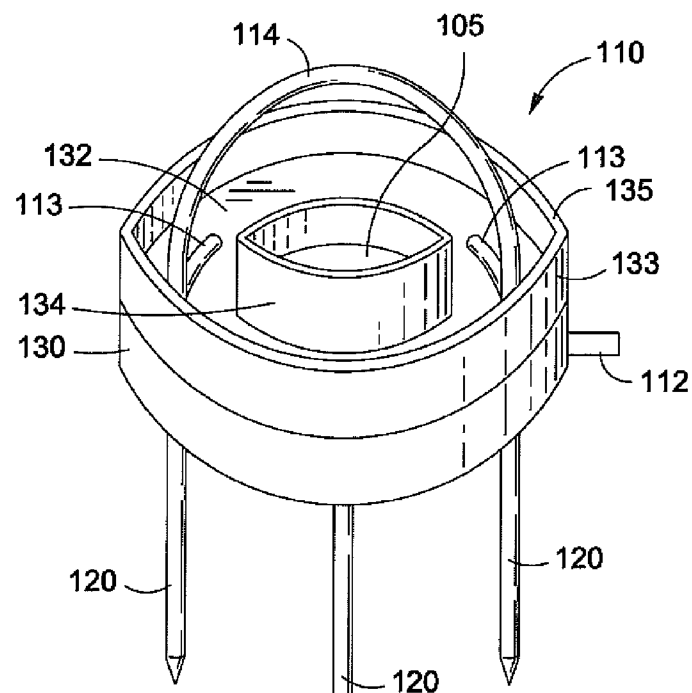
FIG. 1 illustrates a perspective view of an implantable injection port according to an embodiment of the present invention.
Figure 2:
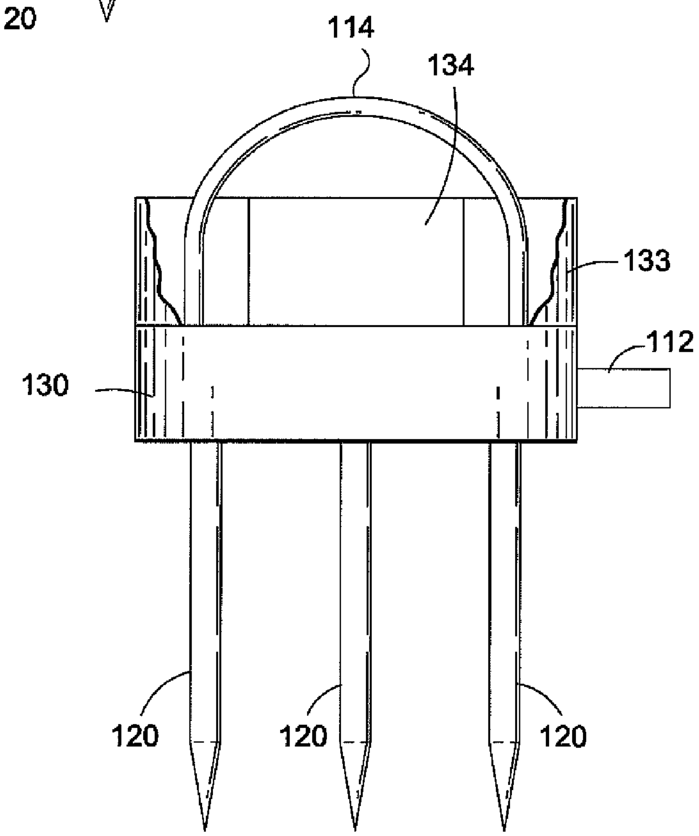
FIG. 2 illustrates a side, cut-away view of the embodiment illustrated in FIG. 1.

Turning now to FIGS. 1 and 2, an implantable injection port 110 comprises a base 130 with a plurality of anchor devices 120 (e.g., anchor needles or anchor pins) passing through openings and/or holes in the base 130 and protruding from the base 130. The anchor devices 120 protrude into the tissue of a patient, for example, into the rectus muscle sheath, so that the port 110 may be implanted into the patient. The port 110 may comprise any number of anchor devices 120 in order to facilitate secure implantation of the port 110. An exit port 112 delivers fluid via flexible tubing to a gastric band.

The port 110 further comprises a shell 133 and a base shaft 134 that both guide a cap 132 as it moves up and down with respect to the base 130. For example, the cap 132 may be movable between a detached position and an attached position with respect to a patient's tissue. A septum 105 for saline injections is located within the base shaft 134. The septum 105 may comprise any self sealing, needle penetrable material, such as silicone. After implantation of the port 110, a syringe needle may be inserted into the septum 105 to facilitate increasing or decreasing the amount of fluid within the gastric band.

A handle 114 is rotatably attached to the cap 132 and facilitates securing the port 110 within the patient's tissue. A locking rod 113 is located at each end of the handle 114, and the locking rod 113 is substantially perpendicular with respect to the handle 114. The locking rod 113 facilitates locking the cap 132 in a raised position to facilitate securing the port 110 within the patient.

Figure 3:
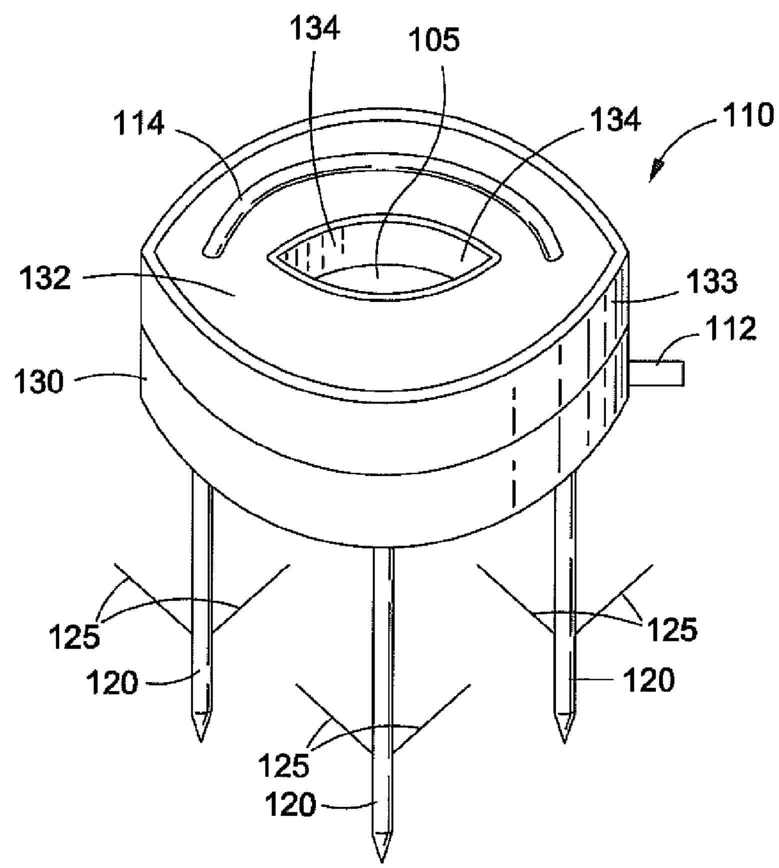
FIG. 3 illustrates another perspective view of an implantable injection port according to the embodiment illustrated in FIG. 1.

In accordance with an embodiment, and with reference to FIG. 3, each anchor device 120 of the port 110 comprises anchor wires 125. The anchor wires 125 protrude into the patient's tissue at an angle that prevents removal of the port 110 from the patient's tissue. The anchor wires 125 emerge from the anchor device 120 into the patient's tissue as the cap 132 moves away from the base 130.

The cap 132 may move away from the base 130 as a doctor pulls on the handle 114, until the top of the cap 132 is substantially flush with the top edge of the shell 133. The handle 114 may then be rotated toward the surface of the cap 132 until it is substantially flush with the surface of the cap 132. The surface of the cap 132 may comprise a recess that receives the handle 114 so that the handle 114 does not protrude above the surface of the cap 132.

Figure 4A:
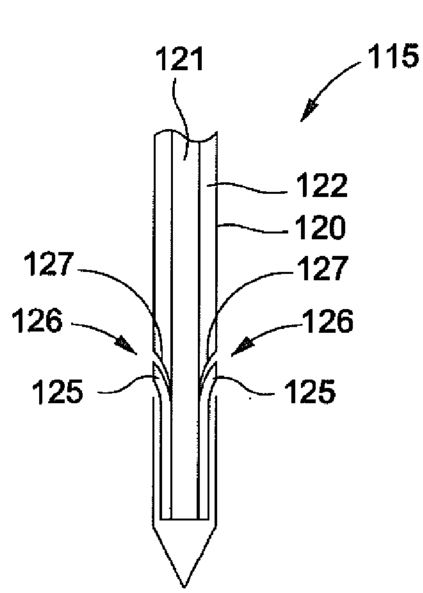
FIGS. 4A-4B illustrate cross-sectional views of an anchoring pin according to the embodiment illustrated in FIG. 1.
Figure 4B:
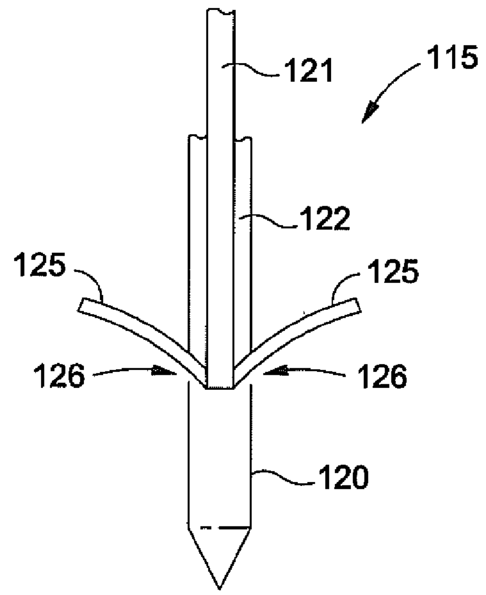

In accordance with various embodiments, and with reference to FIGS. 4A and 4B, the anchor device 120 includes an anchor mechanism 115 for securing the anchor device 120 within the patient's tissue. The anchor mechanism 115 comprises an inner shaft 121 and the anchor wires 125 attach to a portion of the inner shaft 121. The inner shaft 121 is disposed within a cavity 122 of the anchor device 120 and the shaft 121 can move linearly within the cavity 122. In an embodiment, the anchor device 120 has an attachment end coupled to the cap 132 and a free end and/or penetrating end in the shape of a pin. Further, in an embodiment, the anchor device 120 may be formed in the shape of a spiral with a pointed end.

As the shaft 121 moves out of the cavity 122, the anchor wires 125 protrude from the anchor device 120 by passing through anchor openings and/or holes 126 in the anchor device 120. Lips 127 of the anchor device 120 are angled to guide the anchor wires 125 to move out of the anchor device 120. For example, as the shaft 121 moves out of the cavity 122, the lips 127 guide the anchor wires 125 out of the cavity 122. When the anchor wires 125 protrude sufficiently from the anchor device 120, the shaft 121 ceases to move.

Figure 5:
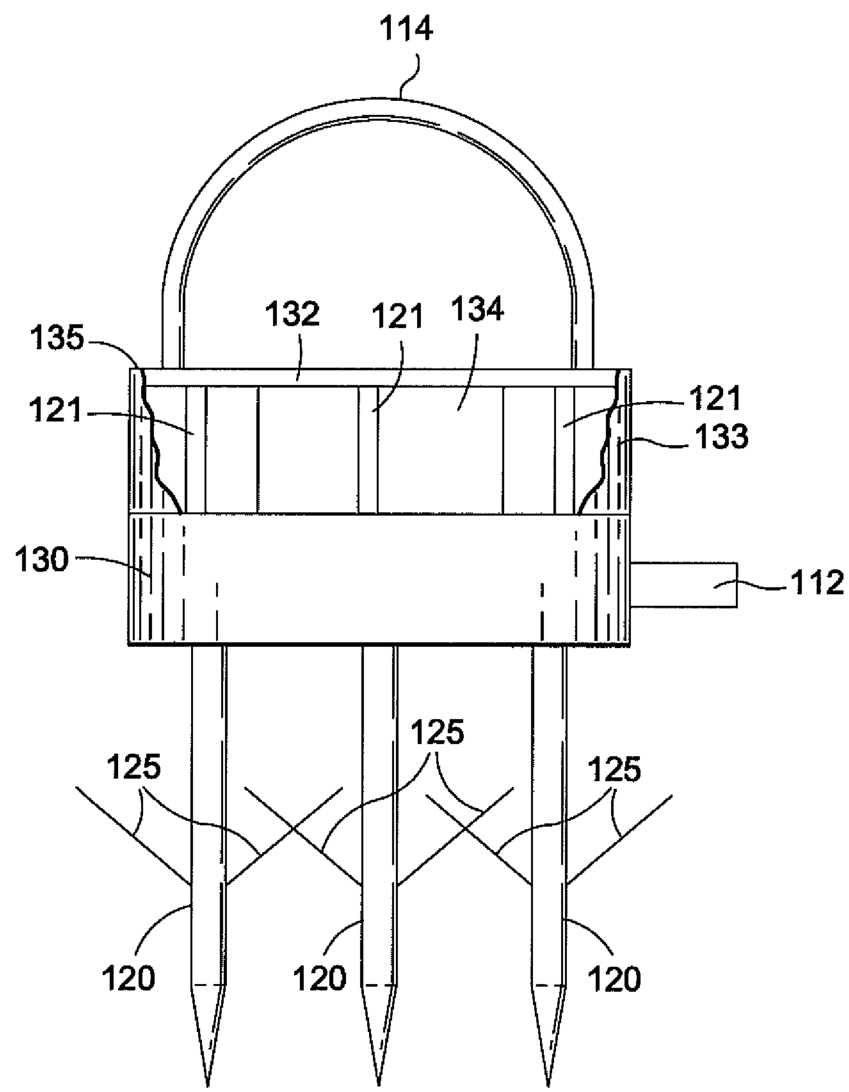
FIG. 5 illustrates another side, cut-away view of the embodiment illustrated in FIG. 1.

With reference to FIG. 5, it can be seen that, in an embodiment, each anchor device 120 includes a shaft 121 and anchor wires 125. The shaft 121 is attached to the cap 132 and is moved out of the anchor device 120 as the cap 132 moves away from the base 130. The cap 132 moves away from the base 130 as force is applied to the handle 114, for example, by a physician's hand and/or by forceps or hemostats. The shell 133 is appropriately dimensioned so that the anchor wires 125 are adequately extended from the anchor device 120 when the cap 132 is substantially flush with a top edge 135 of the shell 133.

Figure 6:
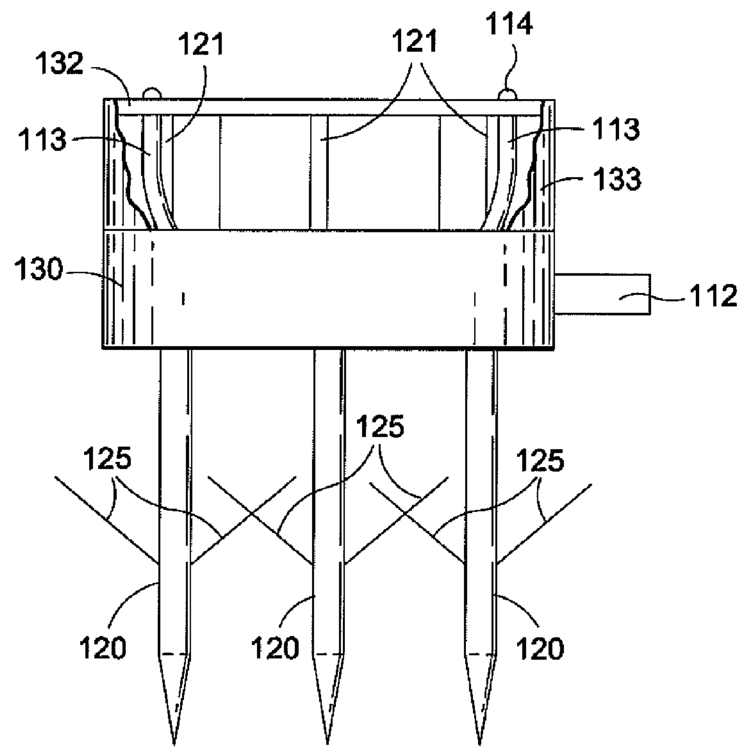
FIG. 6 illustrates yet another side, cut-away view of the embodiment illustrated in FIG. 1.
Figure 7:
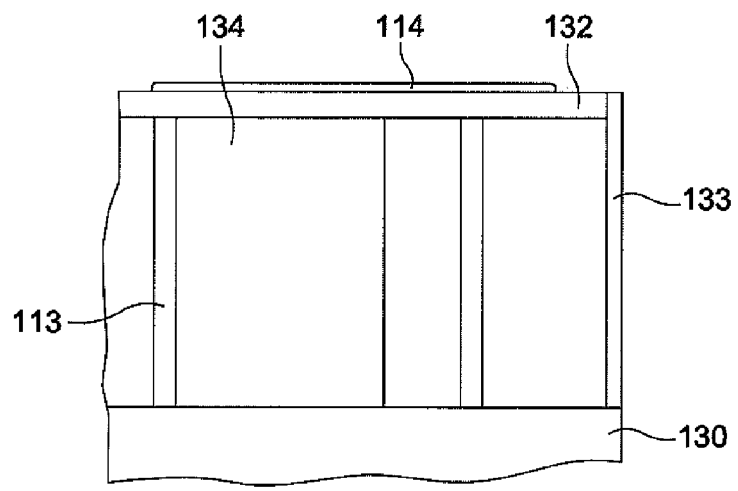
FIG. 7 illustrates a portion of an injection port according to the embodiment illustrated in FIG. 1.
Figure 8:
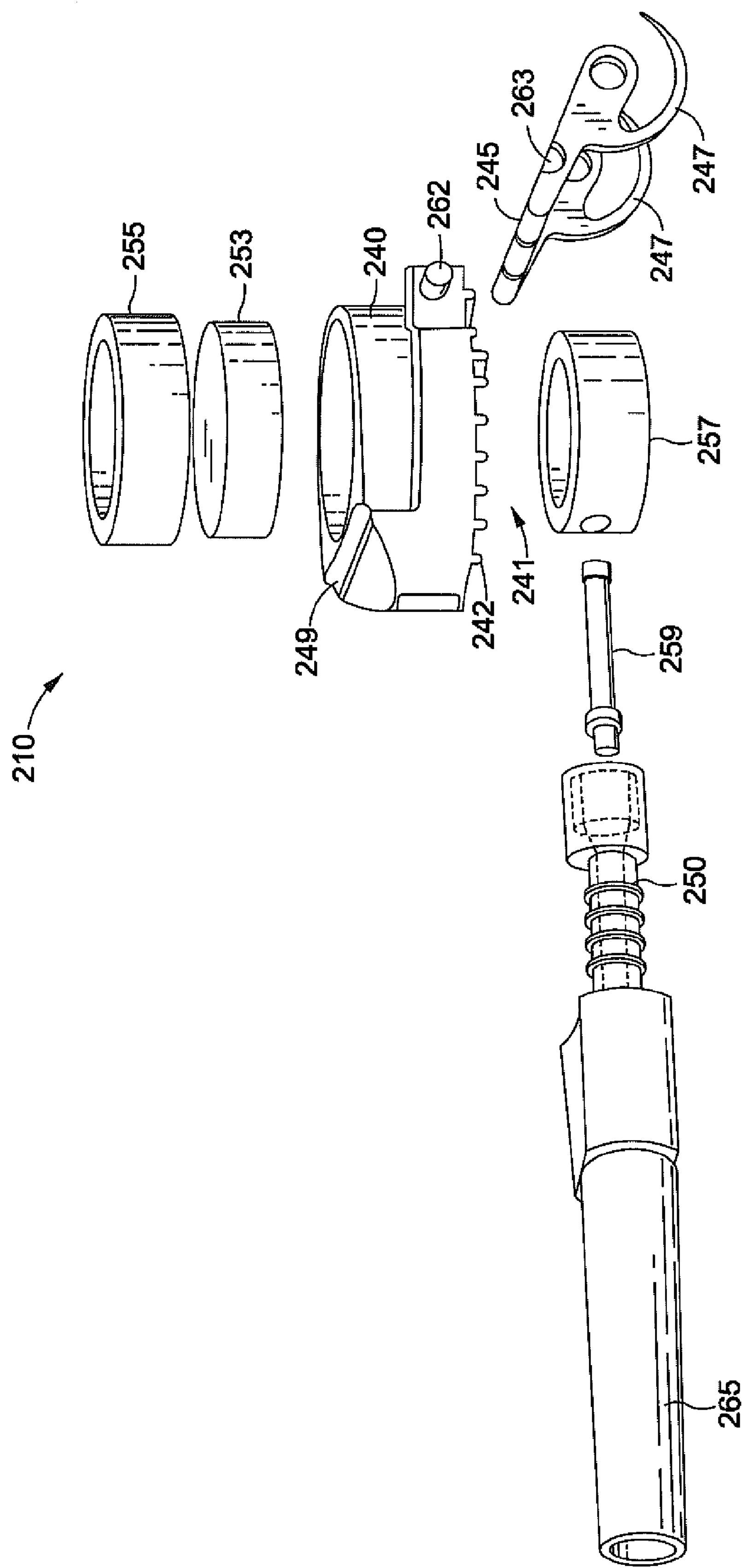
FIG. 8 illustrates an exploded, perspective view of an injection port according to another embodiment of the present invention.
Figure 9:
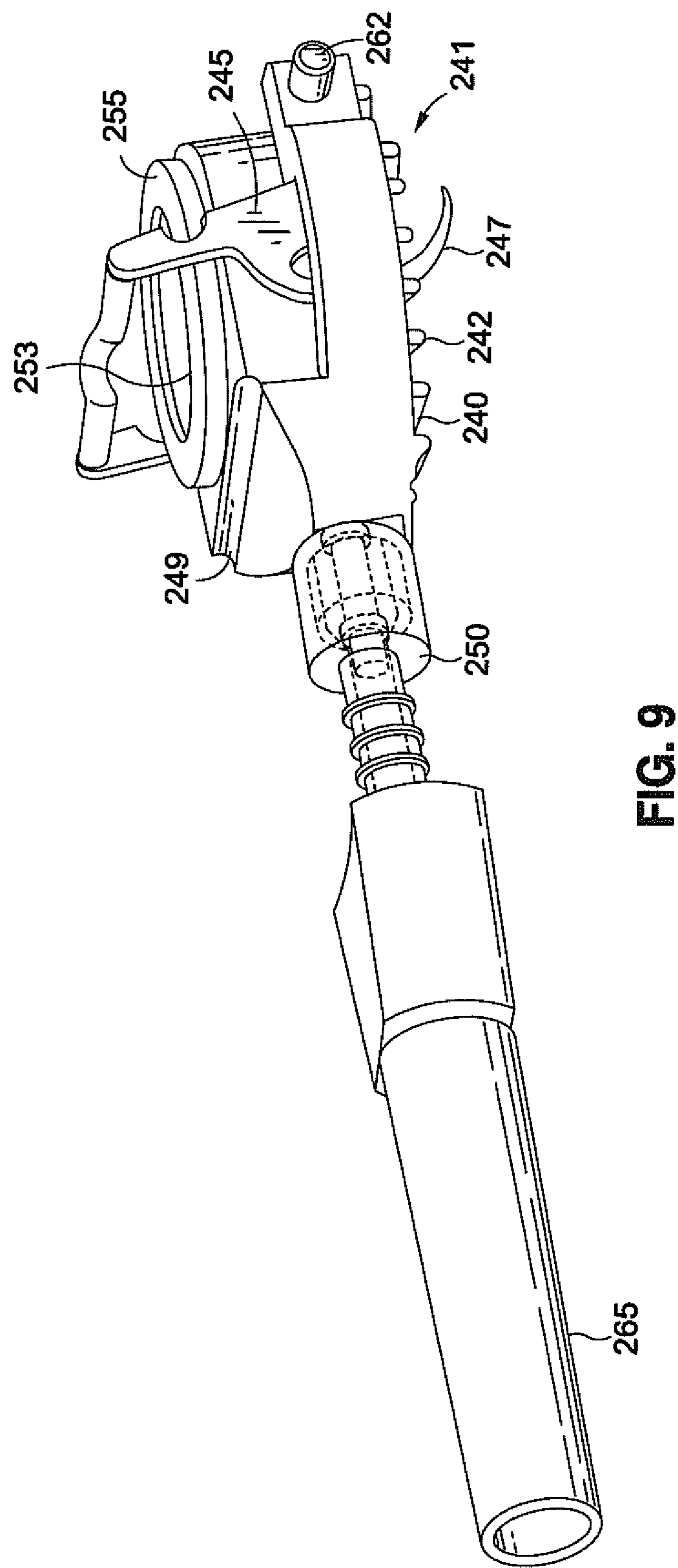
FIG. 9 illustrates a perspective view of the injection port illustrated in FIG. 8.
Figure 10:
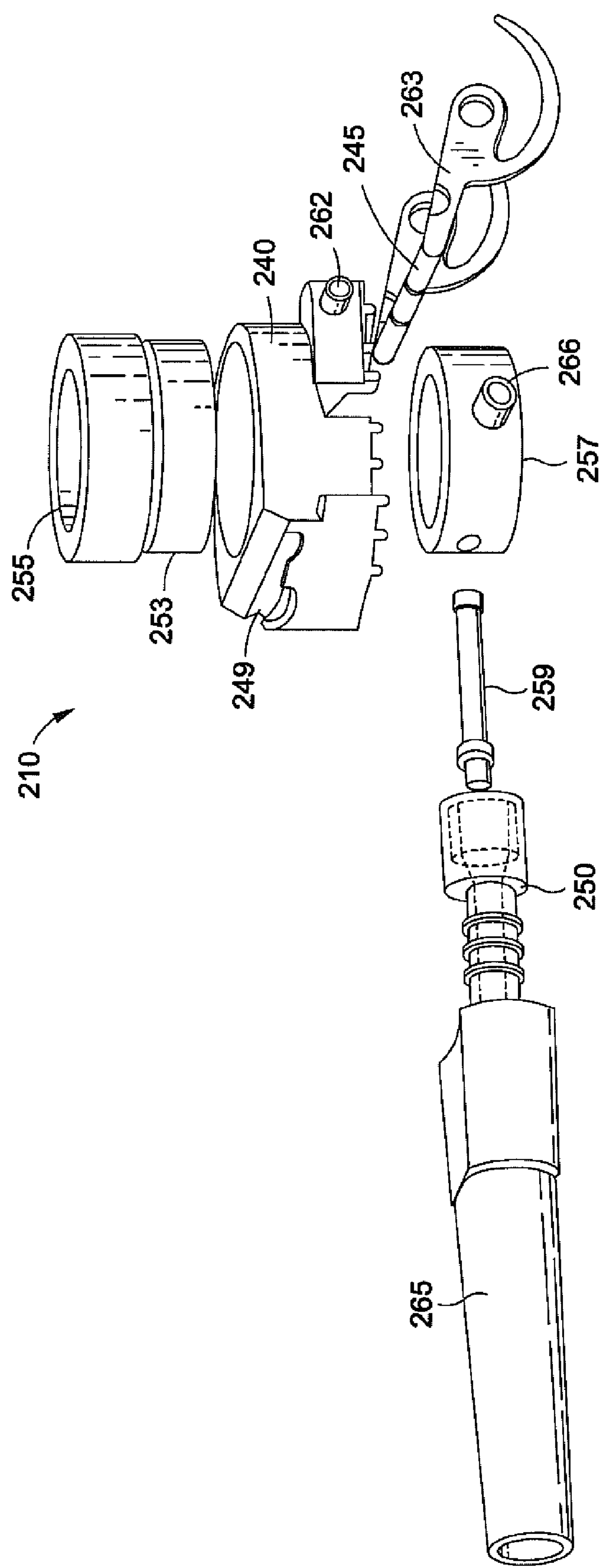
FIG. 10 illustrates an exploded, perspective view of another injection port according to a further embodiment of the present invention.
Figure 11:
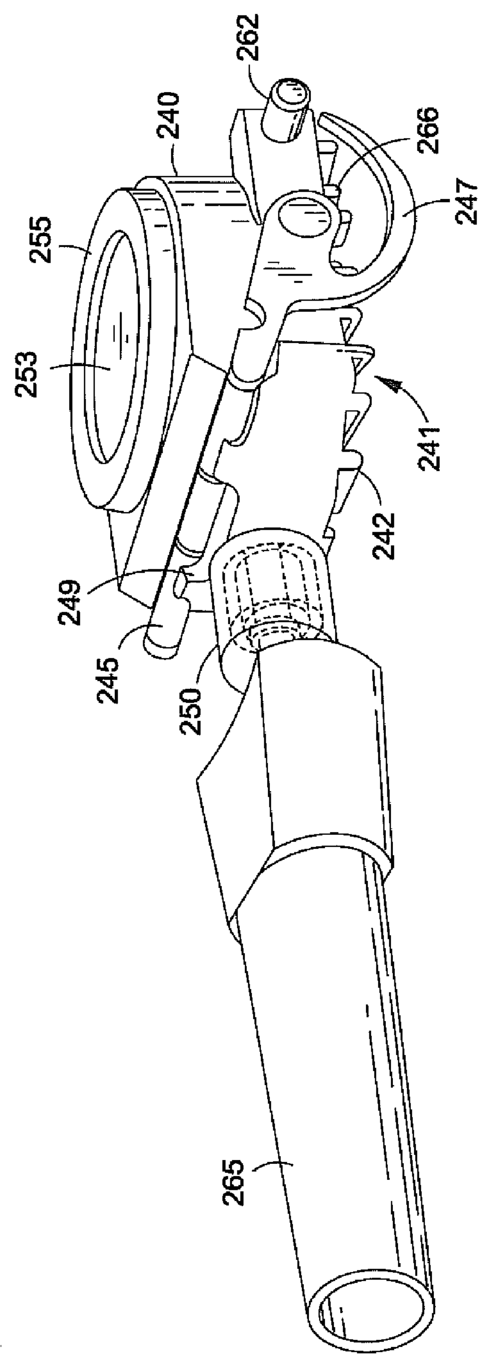
FIG. 11 illustrates a perspective view of the injection port illustrated in FIG. 10.

With reference to FIGS. 6 and 7, once the cap 132 is in the appropriate position with the anchor wires 125 extended, the handle 114 may be locked to prevent the cap 132 from moving toward the base 130. For example, the handle 114 may be rotated towards the cap 132. As the handle 114 rotates, the locking rods 113 rotate toward the base 130, such that when the handle 114 is substantially parallel with the cap 132, the locking rods 113 interface with the base 130.

In various embodiments, the handle 114 may nest within the cap 132 such that an interference and/or press fit is formed between the handle 114 and the cap 132 to prevent the handle 114 from unintentionally rotating out of the cap 132. Further, in an embodiment, the locking rods 113 may fit within a detent, notch and/or catch within the base 130 to prevent the locking rods 113 from unintentionally moving out of the base 130. For example, the cap 132 and/or the base 130 may be described as having a center opening and an outer portion surrounding the center opening, the outer portion having a fitting for securing the handle 114 adjacent to the cap 132. As noted above, the fitting may be at least one of a detent, notch or catch that forms a press-fit and/or interference fit with the locking rods 113 and/or the handle 114.

When the locking rods 113 and/or the handle 114 are in a locked position, the locking rods 113 prevent the cap 132 from moving toward the base 130, thereby preventing the anchor wires 125 from unintentionally retracting into the anchor device 120. The locking rods 113 may be substantially perpendicular with respect to the handle 114 so that when the handle 114 is substantially parallel to the cap 132, the locking rods 113 are substantially perpendicular to the cap 132 and the base 130, thereby preventing the cap 132 from moving toward the base 130.

In order to implant the port 110 within a patient, a physician may grip the port 110 on the outside of the base 130 and the shell 132 using the physician's hand, forceps, hemostat, or other standard surgical tool. In various embodiments, the outside of the base 130 and/or the shell 133 may be textured to provide a better gripping surface for the physician. The bottom of the base 130 may be similarly textured, as discussed further below, in order to create a more secure adhesive contact between the base 130 and the patient's tissue.

Gripping the port 110, the physician may then insert the anchor device 120 through the patient's tissue, for example, through the patient's rectus muscle sheath. The anchor device 120 may be constructed to be various lengths depending on the anatomy of the patient. For example, the anchor device 120 may be approximately 1-2 centimeters long in an embodiment where the port 110 is approximately 2 centimeters in diameter.

Once the port 110 is in place, the physician may pull on the handle 114 using the physician's hand, forceps, hemostat, and/or other surgical tool. Pulling on the handle 114 causes the anchor wires 125 to emerge from the anchor device 120 and move into the patient's tissue. In such a configuration, the port 110 is restricted from moving out of the patient's tissue. The physician may then rotate the handle 114 toward the cap 132 to facilitate locking the handle 114, the cap 132 and the anchor wires 125 in place. The physician may feel a toggling action when a press fit and/or interference fit is created between the handle 114 and the cap 132 and/or between the locking rods 113 and the base 130.

The port 110 may be removed without substantial tissue damage by unlocking the handle 114 and rotating the handle 114 away from the cap 132. The handle 114 and/or the cap 132 are then pressed, causing the cap 132 to move toward the base 130. This motion causes the anchor wires 125 to return into the cavity 122 of the anchor device 120 so that the port 110 may be removed from the patient. Because the physician may insert and remove the port 110 without specialized equipment, implantable ports according to embodiments of the present invention overcome difficulties associated with the prior art.

Turning now to FIGS. 8-11, an implantable injection port 210 comprises curved anchors 247 attached to a handle 245 that may be rotated with respect to a base 240 to facilitate implanting the curved anchors 247 into the tissue of a patient. Although two anchors 247 are described herein, it should be understood that other numbers of anchors 247 may be utilized to facilitate appropriately implanting the injection port 210. Furthermore, it should be understood that the anchors 247 may be of various lengths and may have different curvatures depending on various parameters, such as anticipated force to which the injection port 210 will be subjected and physical characteristics of the area of the patient in which the injection port 210 will be located.

The port 210 further comprises a reservoir 257 disposed within the base 240 to hold a fluid and dispense the fluid into the gastric band. The fluid may be introduced into the reservoir 257 via an injection through a self-sealing septum 253 located proximate to the reservoir 257 and disposed within the base 240. The base 240, in various embodiments, comprises a needle impenetrable housing to prevent an injection needle from damaging the injection port 210. A cap 255 covers the septum 253 and is attached to the base 240.

A discharge port, for example, a port tubing 259, is connected to the reservoir 257. A quick-connect and strain relief fitting 250 is coupled to the port tubing 259 and to the gastric band tubing 265. As is discussed further below, the quick-connect and strain relief fitting 250 facilitates easier, quicker connection of the port 210 to the gastric band tubing 259, and it also prevents leakage from the junction between the fitting 250 and the tubing 259 as the injection port 210 is subjected to movement.

The handle 245 is attached to a pivot and/or hinge 266 (see, e.g., FIG. 11) located on the base 240. The handle 245 may be rotated between an undeployed position and a deployed position. In the undeployed position, the anchors 247 are substantially above the attachment surface 241 of the base 240. In the deployed position, the anchors 247 are substantially below the surface 241 of the base 240 in an implanted orientation.

In the undeployed position, a press-fit notch 263 on the handle 245 forms a press-fit with and/or receives press-fit hub 262 on the base 240. This press-fit maintains the anchors 247 in the undeployed position to prevent unwanted movement of the anchors 247. For example, as a physician is positioning the port 210 within the patient, the anchors 247 remain within the base 240 until the port 210 is in the appropriate location. A press-fit may also be utilized to maintain the anchors 247 in a deployed position within a patient's tissue.

Due to the slippery environment where the port 210 is intended to be located, it may be difficult to hold the port 210 in a desired position during implantation of the anchors 247. The attachment surface 241 and/or other surfaces of the port 210 may comprise various textures, as discussed further below, to increase friction between the patient's tissue and the attachment surface 241 and facilitate more accurate placement of the port 210.

In accordance with various embodiments, suture tabs 242 may be located on the base 240 of the port 210. The suture tabs 242 may provide an additional mechanism for securing the port 210 to the patient together with and/or separately from implantation of the anchors 247.

Figure 12:
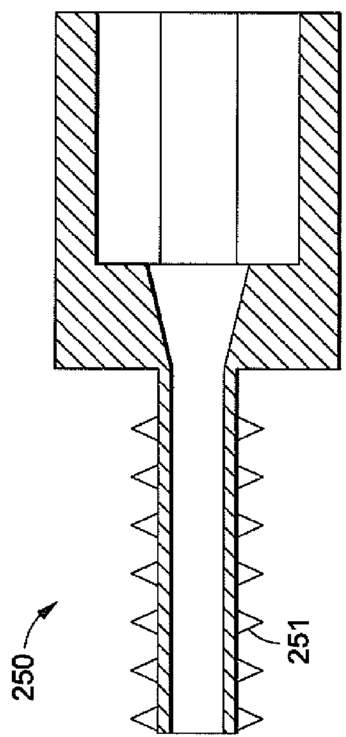
FIG. 12 illustrates a cross-sectional view of a quick-connect and strain relief mechanism according to an embodiment of the present invention.
Figure 13:
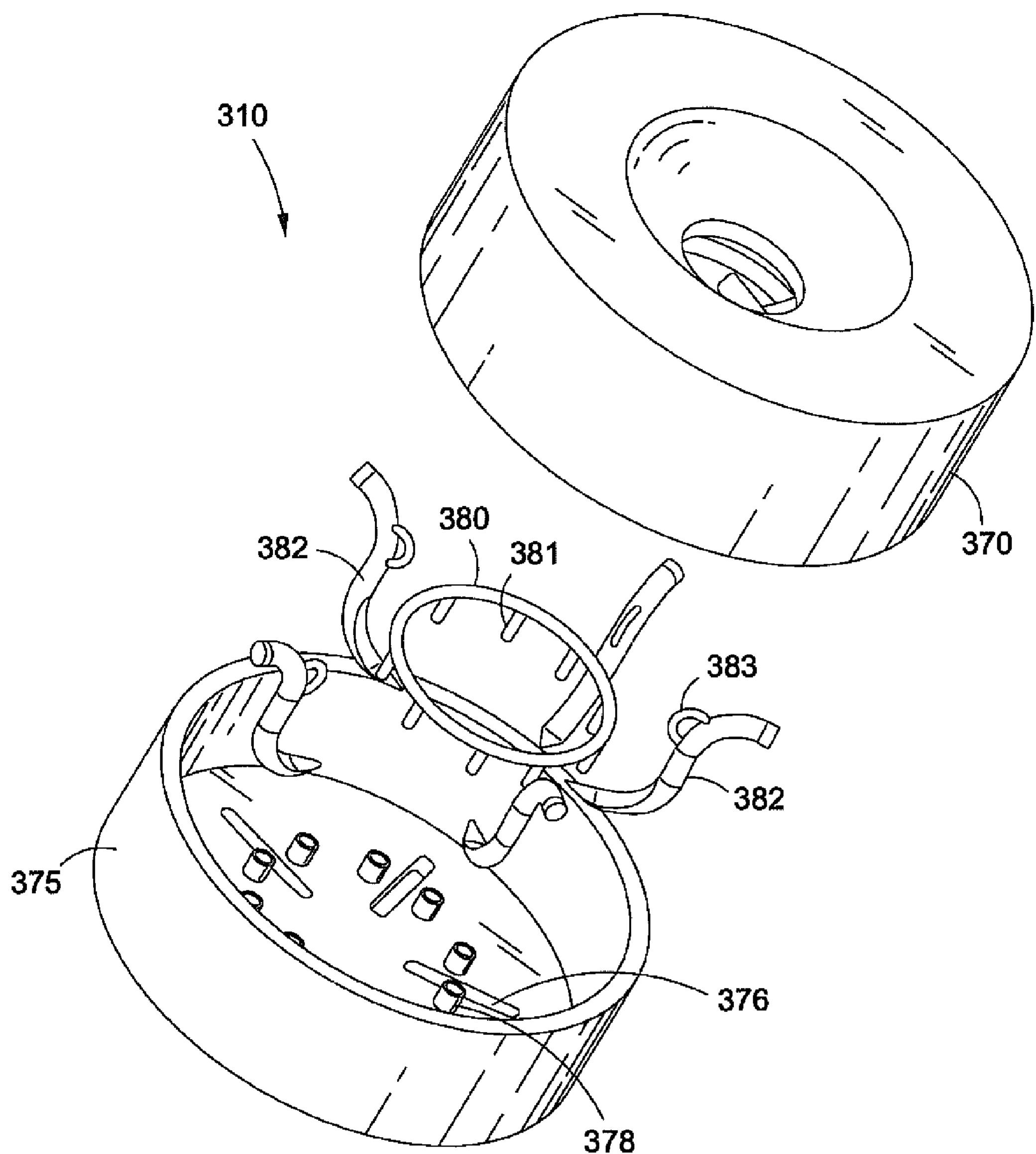
FIG. 13 illustrates an exploded, perspective view of an implantable injection port according to yet another embodiment of the present invention.
Figure 14:
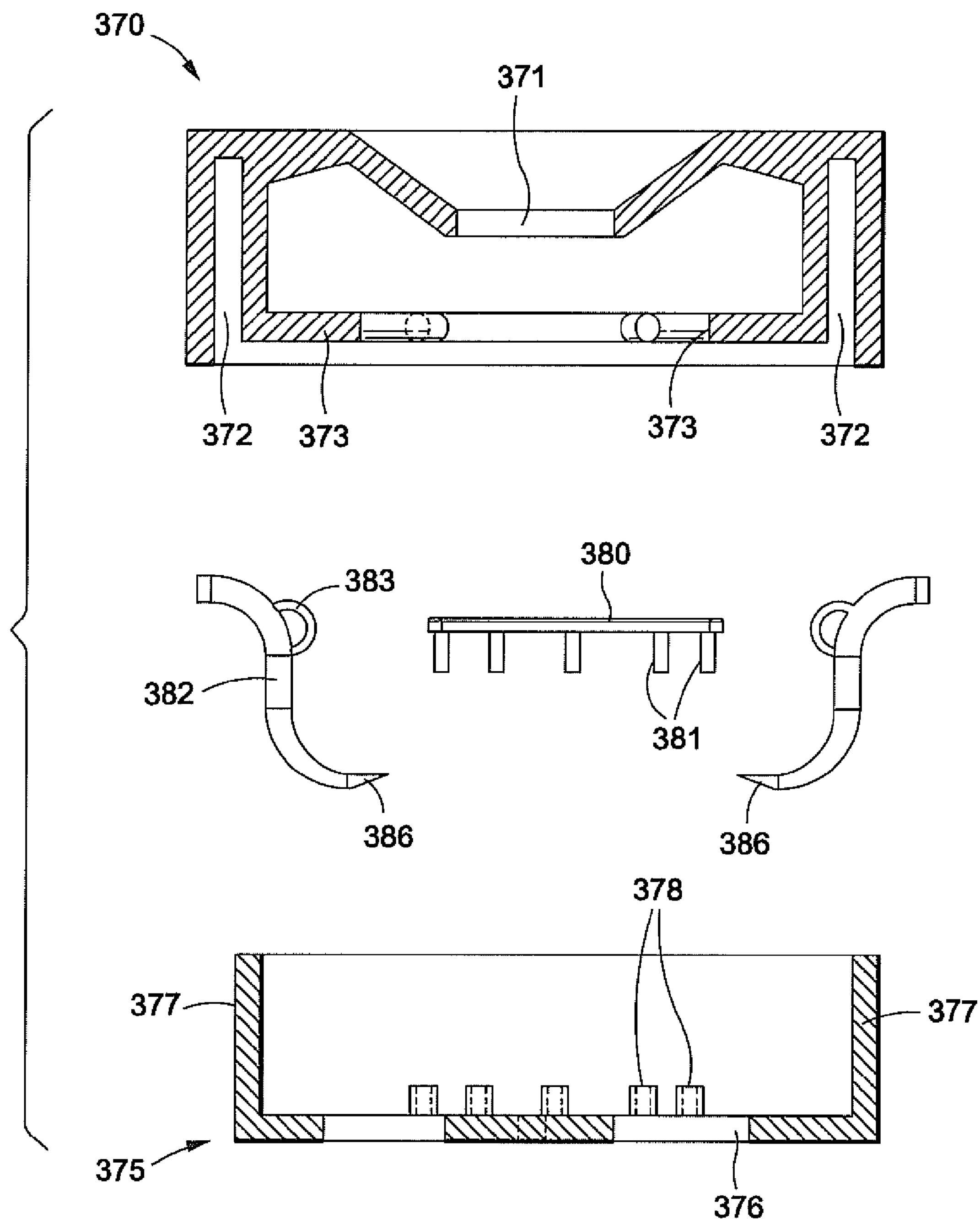
FIG. 14 illustrates an exploded, cross-sectional view of the injection port illustrated in FIG. 13.

FIG. 12 illustrates a cross section of the quick-connect and stress relief fitting 250. The section of the fitting 250 with the larger diameter receives the port tubing 259 from the port 210. The section of the fitting 250 with the smaller diameter interfaces with the gastric band tubing 265. The smaller diameter portion comprises a plurality of flanges 251 that create a sealed connection with the gastric band tubing 265. As the gastric band tubing 265 flexes, the fitting 250 also flexes, and the flanges 251 facilitate maintaining contact between the fitting 250 and the gastric band tubing 265 during such motion to prevent leakage of the fluid being transported from the port 210 to the gastric band.

Furthermore, the fitting 250 makes it easier to connect the port 210 to the gastric band tubing 265 than to make similar connections with existing implantable injection ports. For example, existing ports generally include a substantially rigid discharge port, and the tubing leading to the gastric band is manipulated to fit around the rigid discharge port. The fitting 250, according to various embodiments, is more flexible than the standard discharge ports. Furthermore, the flanges 251 are pliable such that the fitting 250 may be more readily inserted into the gastric band tubing 265, rather than attempting to stretch the tubing 265 around the discharge port.

Releasing the handle 245 from the press-fit hub 262 in the undeployed position, and moving it over the port 210 deploys the anchors 247 into the patient's tissue. This motion may be carried out using a physician's hand, thumb, forefinger, and/or with common operating room equipment such as hemostats or forceps. In the deployed position, the handle 245 is locked using nibs 249. For example, the nibs 249 may be located on either side of the base 240 and may slide into notches on either side of the handle 245. An audible sound and/or tactile feedback may be utilized to confirm that locking has occurred.

Turning now to FIGS. 13-22, an embodiment of an injection port 310 comprises a base 375 that slidably and rotatably nests within a cap 370. As with the other ports discussed above, the port 310 may be utilized to provide fluid to a gastric band and to remove fluid from a gastric band. For example, the port 310 may comprise a fluid port in the base 375 and/or the cap 370 to facilitate providing fluid to, and removing fluid from, a gastric band.

In accordance with various embodiments, a plurality of hooks 382 are circumferentially and rotatably located around a ring 380 that is disposed within the base 375. As the cap 370 slides toward the base 375, the cap 370 interacts with the hooks 382 to cause the hooks 382 to protrude through a plurality of slots 376 in the base 375 into the tissue of a patient. The cap 370 may then be rotated with respect to the base 375 in order to lock the hooks 382 into place.

The port 310 is advantageously configured to allow a physician to implant the port 310 in the patient's tissue without the use of special tools. For example, the port 310 may be implanted using the physician's hand and/or using common operating room tools such as forceps or hemostats. Although variations of the dimensions of the port 310 contemplated within the scope of this disclosure will be apparent to one skilled in the art, in various embodiments, the port 310 is approximately 25-27 millimeters in diameter and approximately 8-10 millimeters in height, and the hooks 382 have a height of approximately 7-10 millimeters.

Figure 15:
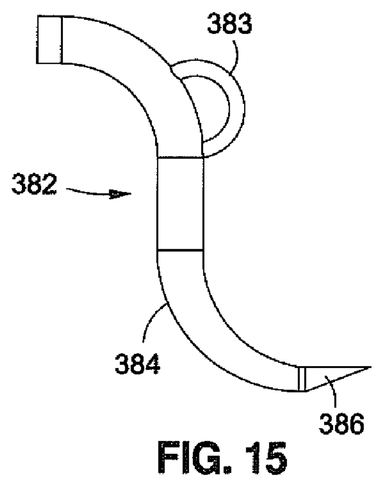
FIG. 15 illustrates a side view of a hook according to an embodiment of the present invention.

With reference to FIG. 15, the hooks 382 have a curvature that facilitates implantation of the hooks 382 into the tissue of a patient. For example, an engagement surface 384 of the hook 382 interacts with the cap 370 as the cap 370 moves towards the base 375, and this interaction causes the hook 382 to enter the patient's tissue.

Figure 16:
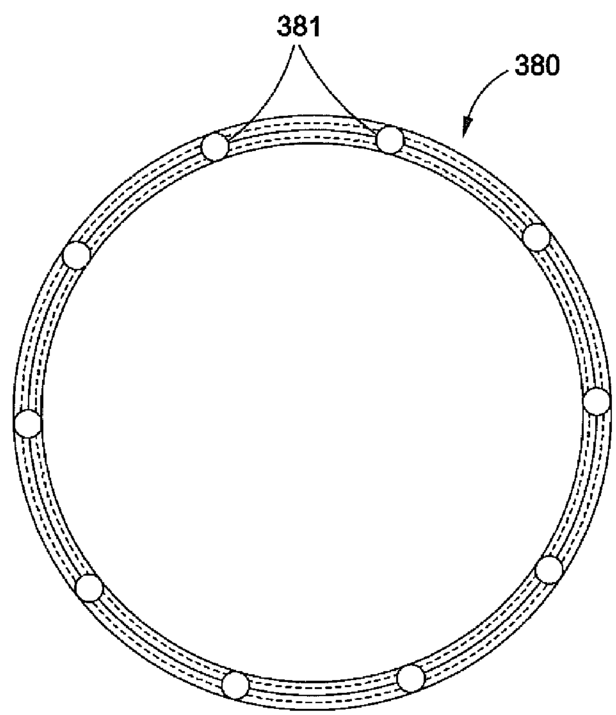
FIG. 16 illustrates a bottom view of an internal ring of the injection port illustrated in FIG. 13.
Figure 17:
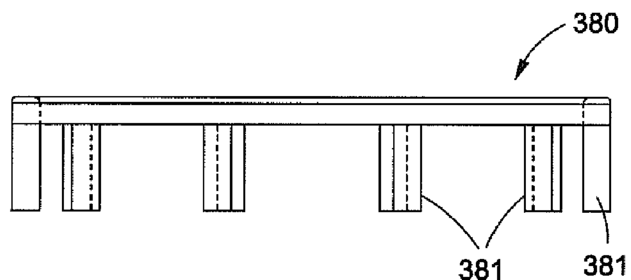
FIG. 17 illustrates a side view of an internal ring of the injection port illustrated in FIG. 13.

With reference to FIG. 16, the hook 382 comprises a loop or eyelet 383 that facilitates connection of the hook 382 to the internal ring 380. A plurality of hooks 382 are circumferentially disposed around the internal ring 380 and are rotatably connected to the internal ring 380 via the eyelets 383. Any number of hooks 382 may be used to secure the port 310 to the patient's tissue. However, in accordance with an embodiment, five hooks 382 may be used.

Figure 18:
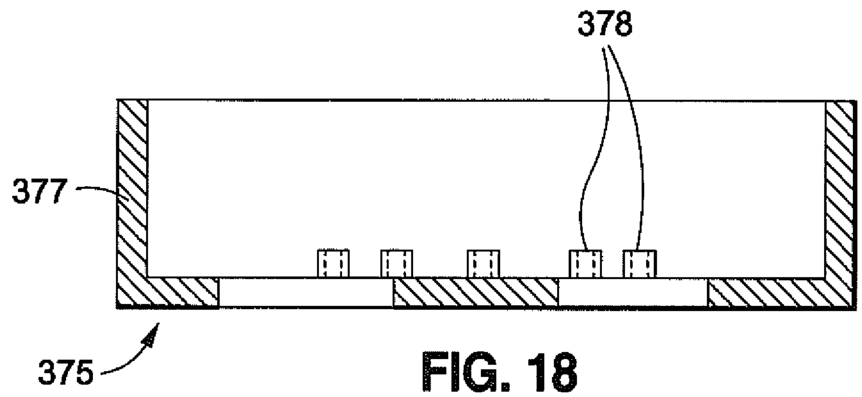
FIG. 18 illustrates a side, cross-sectional view of a base of the injection port illustrated in FIG. 13.

The internal ring 380 comprises a plurality of feet 381 that facilitate connection of the ring 380 to the base 375. With reference to FIG. 18, the base 375 comprises a plurality of apertures or holes 378 configured to receive the plurality of feet 381. In accordance with an embodiment, the plurality of feet 381 are cylindrical and the plurality of holes 378 are also cylindrical and are dimensioned to receive the plurality feet 381 via a press and/or interference fit. It should be understood that the plurality of feet 381 and the plurality of holes 378 may be any complementary geometry that facilitates connection of the ring 380 to the base 375. For example, the plurality of feet 381 may have triangular cross-sections dimensioned for a press-fit in the circular holes 378 in the base 375.

Figure 19:
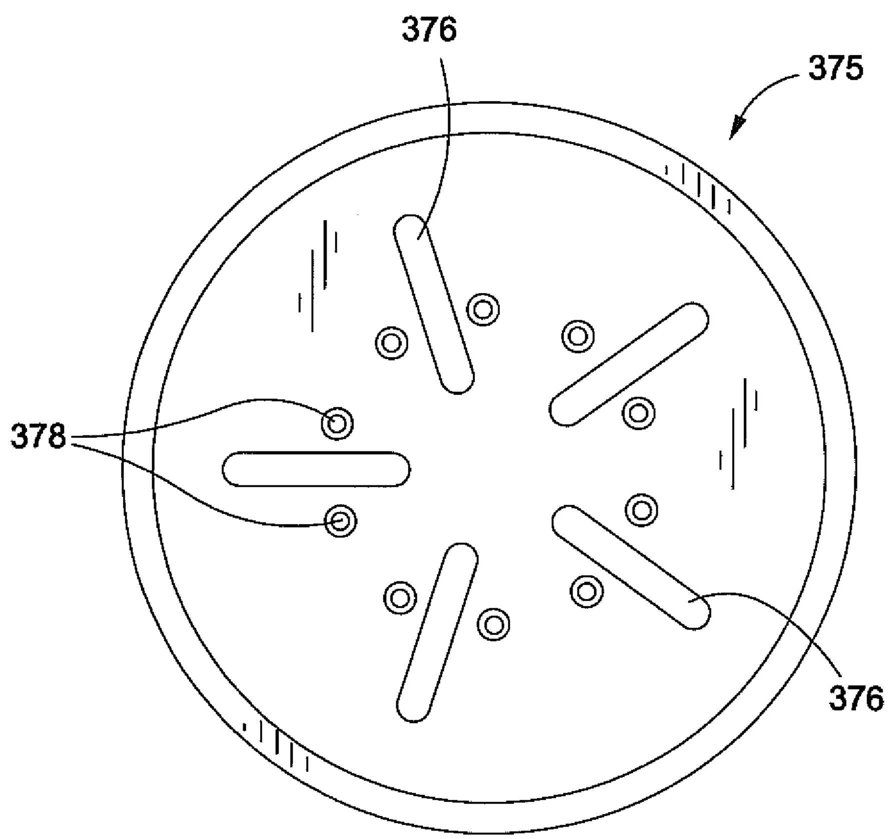
FIG. 19 illustrates a bottom view of a base of the injection port illustrated in FIG. 13.
Figure 20:
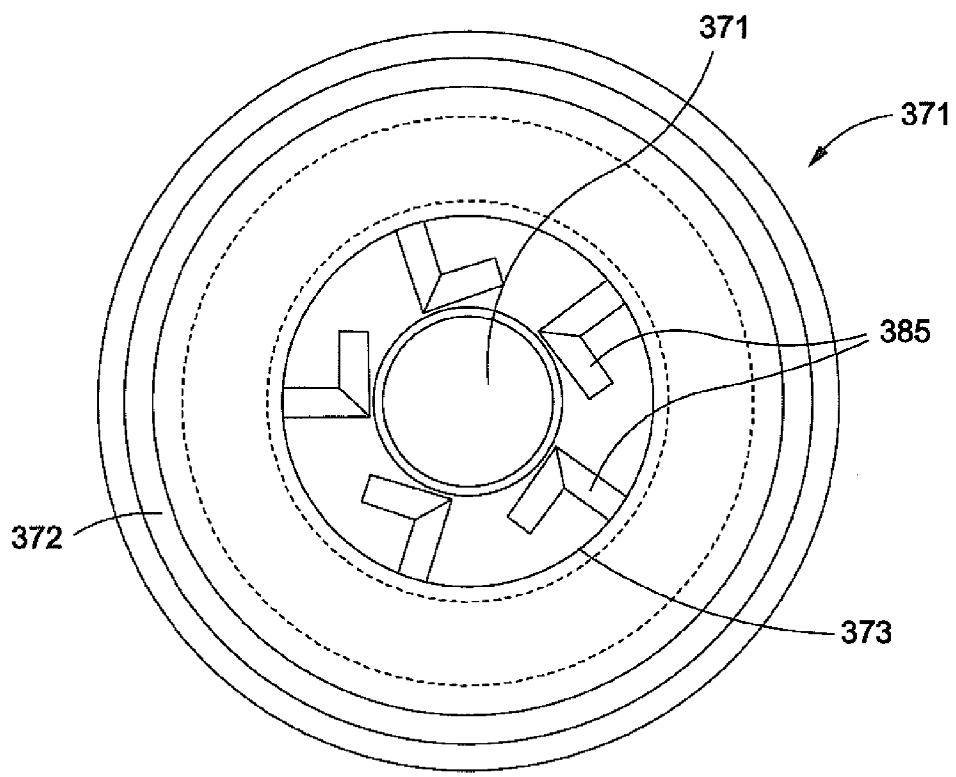
FIG. 20 illustrates a top view of a cap of the injection port illustrated in FIG. 13.
Figure 21:
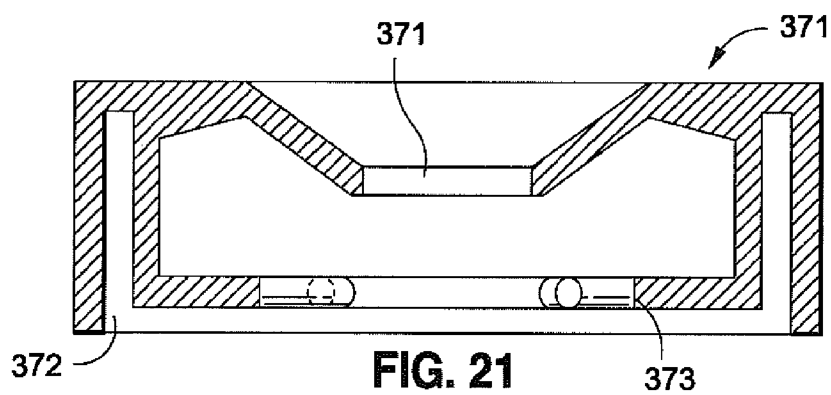
FIG. 21 illustrates a side, cross-sectional view of a base of the injection port illustrated in FIG. 13.

With reference to FIG. 19, the base 375 comprises a plurality of slots 376 through which the plurality of hooks 382 are configured to pass. As illustrated in FIGS. 14 and 16-19, the plurality of hooks 382 and corresponding slots 376 are located between pairs of feet 381 and corresponding holes 378. Thus, in various embodiments, the port 310 comprises one pair of feet 381 and one pair of holes 378 for each hook 382. However, it should be understood that other configurations of feet 381, holes 378, and slots 376 that allow the hooks 382 to rotate about the ring 380 and through the base 375 are contemplated within the scope of the present invention.

With reference to FIGS. 14, 18, and 20-21, the cap 370 is configured to receive the base 375, the ring 380 and the hooks 382. A cylindrical base receiving the slot 372 is circumferentially located near the outside diameter of the cap 370. A corresponding cylindrical cap engagement portion 377 is located near the outside diameter of the base 375. The base receiving slot 372 and the cap engagement portion 377 are dimensioned to allow the base 375 to rotate and/or translate within the cap 370. The cap 370 is configured to allow the hooks 382 to rotate within the port 310 as the cap 370 moves toward and/or away from the base 375.

The cap 370 further comprises a septum hole 371 configured to receive a septum for saline injections. As noted above, the septum may comprise any self-sealing needle-penetrable material, such as silicone. After implantation of the port 310, a syringe needle may be inserted into the septum to facilitate increasing or decreasing the amount of fluid within the gastric band.

Additionally, the cap 370 comprises a cylindrical hook manipulation surface 373 configured to interface with and cause the hooks 382 to extend from the port 310 to penetrate a patient's tissue. As the cap 370 moves towards or away from the base 375, the hook manipulation surface 373 is configured to slide along the hook engagement surface 384 on the hook 382. The curvature of the hook engagement surface 384 causes the hook 382 to rotate about the ring 380 as the hook manipulation surface 373 slides along the hook engagement surface 384. For example, in an embodiment, the hook points 386 are configured to emerge through the slots 376 in the bottom of the base 375 in response to the cap 370 moving towards the base 375. Such a configuration facilitates implanting the hooks 382 into the patient's tissue when the cap 370 moves towards the base 375.

In accordance with various embodiments, the port 310 comprises a locking mechanism configured to lock the hooks 382 and/or the cap 370 into place once the hooks 382 have been implanted in the patient's tissue. For example, the cap 370 may comprise a plurality of hook locking arms 385 spaced circumferentially around the cap 370. The hook locking arms 385 are dimensioned and located within the cap 370 to allow each locking arm 385 to contact each hook 382 in order to prevent movement of the hook 382. For example, the cap 370 may be rotated so that the locking arms 385 may engage the hooks 382 once the hooks 382 have been implanted in the patient's tissue. This configuration facilitates preventing the cap 370 from moving away from the base 375, and preventing the hooks 382 from rotating out of the patient's tissue once the port 310 is in a desired location in the patient.

In accordance with various embodiments, surfaces of the port 310 (and other port embodiments disclosed herein and contemplated by this disclosure) may be textured to facilitate easier and/or more secure implantation of the port 310. The base 375 may be textured to provide better surface adhesion and/or contact between the base 375 and the patient's tissue during installation of the port 310. Furthermore, sides of the port 310 and/or the cap 370 may be textured to allow a physician to grip the port 310 during installation and/or removal of the port 310. Due to the slippery environment where the port 310 is commonly installed, such texture may allow for simpler and/or more accurate placement of the port 310. It should be understood that the same and/or different textures may be used at various locations on the port 310. It should also be understood that similar textures may be utilized in connection with any of the embodiments disclosed herein and/or that are contemplated by this disclosure.

Figure 22:
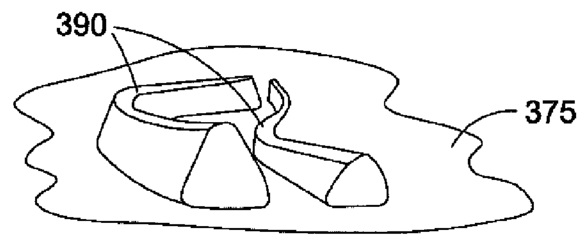
FIG. 22 illustrates a gripping structure according to an embodiment of the present invention.

Although any texture may be used that facilitates appropriate placement of the port 310, in accordance with an embodiment, and with reference to FIG. 22, a gripping structure 390 may comprise substantially parallel, wavy lines that extend over all and/or a portion of the base 375 and/or the cap 370. Such lines may comprise a conical cross-section that increases the contact surface area between the base 375 and the patient's tissue. The increased contact surface area increases the forces that facilitate maintaining the port 310 in a desired location.

In accordance with an embodiment, the gripping structure 390 may comprise papillae projections and/or micro-papillae (similar to hairs (setae) on the feet of geckos) which enhance covalent bonding, van der Waals forces and/or capillary interactions between the base 375 and the patient's tissue. Furthermore, such micro-papillae increase the surface area of contact between the base 375 and the patient's tissue and strengthen the bond therebetween. These micro-papillae may comprise any dimension configured to obtain the results discussed above. In an embodiment, multi-walled carbon nanotubes may be utilized to create such micro-papillae on various surfaces of the port 310.

Further information on such micro-papillae may be found in the following documents, all of which are incorporated herein in their entirety by this specific reference: (1) Yurdumakan B., Raravikar N., Ajayan P., Dhinojawala A. "Synthetic Gecko Foot-Hairs from Multiwalled Carbon Nanotubes." The Royal Society of Chemistry. (2005): 3799-3801; (2) Geim A K., Dubonos S V., Grigorieva I V., Novoselov K S., Zhukov A A., Shapoval S Y. "Microfabricated adhesive mimicking gecko foot-hair." Nature Materials. (2003) 2: 461-463; (3) Autumn K., Sitti M., Liang Y., Peattie A., Hansen W., Sponberg S., Kenny T., Fearing R., Israelachvili J., Full R. "Evidence of van der Waals adhesion in gecko setae." PNAS (2002); 99(19): 12252-12256.

Implantation of the port 310, according to an embodiment, comprises first locating an appropriate place in the patient for implantation of the port 310. The cap 370 is drawn away from the base 375 so that the hooks 382 are substantially within the port 310. Once the port 310 is in a desired location, a physician presses down on the cap 370 using a hand, finger, thumb and/or a common operating room tool. As the physician presses on the cap 370, the hook manipulation surface 373 in the cap 370 acts on the engagement surface 384 of the hooks 382, causing the hooks 382 to rotate with respect to the ring 380 and causing the hook points 386 to penetrate the patient's tissue. Once the hooks 382 have been implanted, the cap 370 is rotated so that the locking arms 385 engage the hooks 382 to prevent the hooks 382 from rotating away from the patient's tissue and to prevent the cap 370 from moving away from the base 375. Removal of the port 310 may be accomplished by following the above steps in reverse. The port 310 may thus be efficiently implanted into and/or removed from a patient's tissue using only a physician's hand and/or common operating room tools.

Unless otherwise indicated, all numbers expressing quantities of ingredients, volumes of fluids, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventors expect skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, certain references have been made to patents and printed publications throughout this specification. Each of the above-cited references and printed publications are individually incorporated herein by reference in their entirety.

Specific embodiments disclosed herein may be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. An implantable injection port for a gastric band and for attaching to bodily tissue, the implantable injection port comprising:

a base having a first opening;

a cap having a handle, the cap moveable between an undeployed position and a deployed position using the handle, the cap spaced apart from the base when in the deployed position;

a first anchor configured to be positioned in the first opening of the base, the first anchor having a cavity, a hole, an inner shaft, and an anchor wire, the inner shaft coupled to the cap such that moving the cap from the undeployed position to the deployed position causes a portion of the anchor wire to move through the hole to be positioned outside the cavity and moving the cap from the deployed position to the undeployed position causes a portion of the anchor wire to move through the hole to be positioned inside the cavity;

an outer shell and an inner base shaft coupled to the base, the cap being guided by and positioned between the shell and the base shaft; and a septum positioned in the base shaft.

2. The implantable injection port of claim 1 wherein the inner shaft moves within the cavity to cause the anchor wire to move through the hole.

3. The implantable injection port of claim 1 wherein the first anchor has an attachment end coupled to the cap and a free end configured in the shape of a pin.

4. The implantable injection port of claim 1 wherein the first anchor has a second hole for passing the anchor wire.

5. The implantable injection port of claim 1 further comprising a locking rod for locking the cap in the undeployed position or the deployed position.

6. The implantable injection port of claim 5 wherein the locking rod is connected to the handle such that rotating the handle locks the locking rod and the handle.

7. The implantable injection port of claim 5, wherein the locking rod extends at an angle with respect to a plane of the handle.

8. The implantable injection port of claim 7, wherein the locking rod extends transverse to the handle.

* * * * *